(12) United States Patent
Wei et al.

(10) Patent No.: US 7,186,812 B2
(45) Date of Patent: Mar. 6, 2007

(54) ISOLATED HUMAN G-PROTEIN COUPLED RECEPTORS, NUCLEIC ACID MOLECULES ENCODING HUMAN GPCR PROTEINS, AND USES THEREOF

(75) Inventors: Ming-Hui Wei, Germantown, MD (US); Fangcheng Gong, Germantown, MD (US); Valentina Di Francesco, Rockville, MD (US); Ellen M. Beasley, Darnestown, MD (US)

(73) Assignee: Applera Corporation, Norwalk, CT (US)

( * ) Notice: Subject to any disclaimer, the term of this patent is extended or adjusted under 35 U.S.C. 154(b) by 980 days.

(21) Appl. No.: 09/820,095

(22) Filed: Mar. 29, 2001

(65) Prior Publication Data

US 2003/0233668 A1    Dec. 18, 2003

(51) Int. Cl.
*C07H 21/02* (2006.01)
*C07H 21/04* (2006.01)

(52) U.S. Cl. .................. 536/23.1; 536/23.2; 536/23.5; 435/320.1; 435/325; 435/455; 435/243; 435/348; 435/353; 435/354; 435/410; 435/358; 435/254.11

(58) Field of Classification Search ............... 536/23.1, 536/23.2, 23.5; 424/93.2; 435/320.1, 325, 435/455, 243, 348, 353, 354, 410, 358, 254.11, 435/252.3
See application file for complete search history.

(56) References Cited

U.S. PATENT DOCUMENTS 5,714,381 A * 2/1998 Bard et al. .................. 435/325
6,214,581 B1   4/2001 Lynch et al.
6,255,472 B1 * 7/2001 Tokino et al. ............. 536/23.5

FOREIGN PATENT DOCUMENTS

WO    WO 98/42835 A1    10/1998

OTHER PUBLICATIONS

Urano et al., "Cloning of P2XM, a Novel Human P2X Gene Regulated by p53." Cancer Research. Aug. 1, 1997. vol. 57, pp. 3281-3287.
International Search Report dated Dec. 19, 2002.
Nawa G et al.; "Frequent Loss of Expression or Aberrant Alternative Splicing of P2XM, A P53-Inducible Gene, in Soft-Tissue Tumours"; British Journal of Cancer, London, GB, vol. 80, No. 8, Jun. 1999, pp. 1185-1189, XP001066564; ISSN: 0007-0920.

* cited by examiner

*Primary Examiner*—Joseph Woitach
*Assistant Examiner*—Brian Whiteman
(74) *Attorney, Agent, or Firm*—Celera Genomics; Justin D. Karjala

(57) ABSTRACT

The present invention provides amino acid sequences of peptides that are encoded by genes within the Human genome, the GPCR peptides of the present invention. The present invention specifically provides isolated peptide and nucleic acid molecules, methods of identifying orthologs and paralogs of the GPCR peptides and methods of identifying modulators of the GPCR peptides.

9 Claims, 14 Drawing Sheets

```
   1 TTGCTGACTC ATGTGCCCGC AGCTAGCAGG AGCTGGCAGC ATGGGCTCCC
  51 CAGGGGCTAC GACAGGCTGG GGGCTTCTGG ATTATAAGAC GGAGAAGTGG
 101 GCTCTCCTCG CCAAAAAAGG CTACCAGGAG CGGGACCTGG AACCCCAGTT
 151 TTCCATCATC ACCAAACTCA AAGGGGTTTC CGTCACTCAG ATCAAGGAGC
 201 TTGGAAACCG GCTGTGGGAT GTGGCCGACT TCGTGAAGCC ACCTCAGGGA
 251 GAGAACGTGT TCTTCTTGGT GACCAACTTC CTTGTGACGC CAGCCCAAGT
 301 TCAGGGCAGA TGCCCAGAGC ACCCGTCCGT CCCACTGGCT AACTGCTGGG
 351 TCGACGAGGA CTGCCCCGAA GGGGAGGGAG GCACACACAG CCACGGTGTA
 401 AAAACAGGCC AGTGTGTGGT GTTCAATGGG ACCCACAGGA CCTGTGAGAT
 451 CTGGAGTTGG TGCCCAGTGG AGAGTGGCGT TGTGCCCTCG AGGCCCTGC
 501 TGGCCCAGGC CCAGAACTTC ACACTGTTCA TCAAAAACAC AGTCACCTTC
 551 AGCAAGTTCA ACTTCTCTAA GTCCAATGCC TTGGAGACCT GGGACCCCAC
 601 CTATTTTAAG CACTGCCGCT ATGAACCACA ATTCAGCCCC TACTGTCCCG
 651 TGTTCCGCAT TGGGACCTC GTGGCCAAGG CTGGAGGGAC CTTCGAGGAC
 701 CTGGCGTTGC TGGGTGGCTC TGTAGGCATC AGAGTTCACT GGGATTGTGA
 751 CCTGGACACC GGGGACTCTG GCTGCTGGCC TCACTACTCC TTCCAGCTGC
 801 AGGAGAAGAG CTACAACTTC AGGACAGCCA CTCACTGGTG GGAGCAACCG
 851 GGTGTGGAGG CCCGCACCCT GCTCAAGCTC TATGGAATCC GCTTCGACAT
 901 CCTCGTCACC GGGCAGGCAG GGAAGTTCGG GCTCATCCCC ACGGCCGTCA
 951 CACTGGGCAC CGGGGCAGCT TGGCTGGGCG TGGTCACCTT TTTCTGTGAC
1001 CTGCTACTGC TGTATGTGGA TAGAGAACGC CATTTCTACT GGAGGACAAA
1051 GTATGAGGAG GCCAAGGCCC CGAAAGCAAC CGCCAACTCT GTGTGGAGGG
1101 AGCTGGCCCT TGCATCCCAA GCCCGACTGG CCGAGTGCCT CAGACGGAGC
1151 TCAGCACCTG CACCCACGGC CACTGCTGCT GGGAGTCAGA CACAGACACC
1201 AGGATGGCCC TGTCCAAGTT CTGACACCCA CTTGCCAACC CATTCCGGGA
1251 GCCTGTAGCC GTTCCCTGCT GGTTGAGAGT TGGGGGCTGG GAAGGGCGGG
1301 GCCCTGCCTG GGGATCTCAA GGATGAGGCC CCAGCATGGA GGATTGGGGG
1351 TAGAATTCCA CCCTTGAACC CCAGCAGACA GTCCCTCCCC TGACTCCCAC
1401 CTTGGTAGGG TGCTGCCTCA GGGAGCCATA GAAGTCGGCT GTGTTTTGAG
1451 ACGGCGACAG AACCTGACCC GTGGAGACTG GGAGAGCCCA GCAGGCACCT
1501 GTATTGCAGG GCTCCGACTG CATGTGGCAG GGGCTCCTGC TGCGTCTGGG
1551 CCTGGAGGTC TCTCTCCCAG TGCTCTGTCC CCAGTGTTCC TAGCAGAGGT
1601 ATGCTTACCA GCTGTCAGCA CAGACCCTCC TGCTGCCTGG GTCCTGGCCC
1651 TCCTCCCCCA TCTGCACCCC CATCATAGGT AGAGACCCCA CCCTCCCATC
1701 GGTCCTACAT GGGGCTGTGC AGCTGGAGCC AAAAAGGCAA GGCAGAAAGA
1751 GGAGTGATGG GGGAGGGGGA TTGTTTCAGC TTCTCTGGTG CTGTGATGCC
1801 CCAGGAGAGT CCTAATCTAG GGAATGGGGT GGAGTAGGCA GATAATCCAC
1851 CTCCCTATCC CCCAGGCAAG GGCGGAGCAT GTGTCTTGGG CCCACACCTG
1901 CTTAGTTTAT GAGGACCGGC TGCTTTCCAG TGGTAGCCCT TTTGCCATGG
1951 AGGTCTGGGA GAGAGAGCAG AGGGCGGCAG GGCTAAGTTG GTGATCATTG
2001 GGTTCTTCAG GACCTTCTAT ATCCCTCCTC GGTAACCCCC CAGCCCAACC
2051 CCTTGGAATC TTTCCTCCAG GCTTCCTGAG AGCCCTGGGG GTGGGAGGCT
2101 GTGGGAGGCT GTACATCTGA AATTCACTTC AGTCCAAGTC ATACCTAGGA
2151 AGCTGTCTGG GCAGCTGCTC GAGGGAGGCC CTGGCTCTGA TCCCAGGCTG
2201 GATGGAGTGG CTGGAAGGAA TGGTTCCAAA CAACACCACC GAGATCTCCC
2251 TCAGGCTGGC CAGGTTTTGC AGCTGGAATT CTCCTCTTGG TCCCAGGGCG
2301 GGGCAGGGAA TTCTAAGTGT CCACCCCAGG GAGGCAAGGG GCTGCTTTCC
2351 ACTGTGGGTA CCTGGTGATC AGGGCAAGCT GTGGAGGGCA AGGGGTGGGG
2401 CTGAGACTGG GCTGACATCT AGAATCACCT GCCACCTGGA GCCTCAGTAA
2451 AATGCCTGGG GTCCCTGCTG CCTCTCAATC TCCAGAGCCA TGTCCATGGG
2501 GAGGTGGGCT CTGAAGGGCG AAGGTGGGAG AGCAGGGCCC CTGAGGCCTG
2551 GGTATCCAAG GAGGGGCACG TGCACCTGAT TCTCCTTGGG GCCCAGAGGA
2601 AGCTGATGTC ATGGCTGGAC AAAGTCACGG AGTAAAGCCA GCAAAGCCAC
2651 CAAAAAAAAA AAAAAAAAAA AAAAAAAAAA AAAAAAAAAA AAA
  (SEQ ID NO: 1)
```

FEATURES:
5'UTR:       1 - 40
Start Codon: 41
Stop Codon:  1256
3'UTR:       1259

FIGURE 1A

HOMOLOGOUS PROTEIN:
Top 10 BLAST Hits:

```
                                                                   Score      E
Sequences producing significant alignments:                        (bits)   Value
CRA|18000005098398 /altid=gi|4885535 /def=ref|NP_005437.1| puri...   857     0.0
CRA|335001098681202 /altid=gi|11417813 /def=ref|XP_009854.1| pu...   857     0.0
CRA|1000682348238 /altid=gi|6469324 /def=gb|AAF13303.1|AF065385...   855     0.0
CRA|18000005129684 /altid=gi|6754966 /def=ref|NP_035158.1| puri...   621     e-177
CRA|18000005027891 /altid=gi|6981322 /def=ref|NP_036853.1| p2X6...   604     e-172
CRA|148000001425983 /altid=gi|7920253 /def=gb|AAF70599.1|AF2050...   360     2e-98
CRA|18000005038217 /altid=gi|7447773 /def=pir||S71344 purinergi...   348     8e-95
CRA|18000005027890 /altid=gi|1709522 /def=sp|P51578|P2X5_RAT P2...   345     7e-94
CRA|18000005064403 /altid=gi|4505549 /def=ref|NP_002551.1| puri...   318     9e-86
CRA|18000005196095 /altid=gi|4099121 /def=gb|AAD00553.1| (U8399...   318     9e-86
```

EST:

```
                                                     Score      E
Sequences producing significant alignments:          (bits)   Value
gi|11617343 /dataset=dbest /taxon=96...               1164     0.0
gi|6992441  /dataset=dbest /taxon=960...               648     0.0
gi|4990980  /dataset=dbest /taxon=9606 ...             579     e-163
gi|10325489 /dataset=dbest /taxon=96...                464     e-128
gi|2195075  /dataset=dbest /taxon=9606 ...             287     4e-75
```

EXPRESSION INFORMATION FOR MODULATORY USE:
gi|11617343 Brain- anaplastic oligodendroglioma
gi|6992441  Chronic lyphocytic leukemia
gi|4990980  Lung- carcinoid
gi|10325489 lung - large cell carcinoma
gi|2195075  Colon Tissue expression:
Whole brain

FIGURE 1B

```
  1 MGSPGATTGW GLLDYKTEKW ALLAKKGYQE RDLEPQFSII TKLKGVSVTQ
 51 IKELGNRLWD VADFVKPPQG ENVFFLVTNF LVTPAQVQGR CPEHPSVPLA
101 NCWVDEDCPE GEGGTHSHGV KTGQCVVFNG THRTCEIWSW CPVESGVVPS
151 RPLLAQAQNF TLFIKNTVTF SKFNFSKSNA LETWDPTYFK HCRYEPQFSP
201 YCPVFRIGDL VAKAGGTFED LALLGGSVGI RVHWDCDLDT GDSGCWPHYS
251 FQLQEKSYNF RTATHWWEQP GVEARTLLKL YGIRFDILVT GQAGKFGLIP
301 TAVTLGTGAA WLGVVTFFCD LLLLYVDREA HFYWRTKYEE AKAPKATANS
351 VWRELALASQ ARLAECLRRS SAPAPTATAA GSQTQTPGWP CPSSDTHLPT
401 HSGSL (SEQ ID NO: 2)
```

FEATURES:
Functional domains and key regions:
[1] PDOC00001 PS00001 ASN_GLYCOSYLATION
N-glycosylation site Number of matches: 3
    1    129-132   NGTH
    2    159-162   NFTL
    3    174-177   NFSK

---

[2] PDOC00004 PS00004 CAMP_PHOSPHO_SITE
cAMP- and cGMP-dependent protein kinase phosphorylation site 368-371   RRSS

---

[3] PDOC00005 PS00005 PKC_PHOSPHO_SITE
Protein kinase C phosphorylation site

Number of matches: 2
    1     17-19    TEK
    2    131-133   THR

---

[4] PDOC00006 PS00006 CK2_PHOSPHO_SITE
Casein kinase II phosphorylation site

Number of matches: 2
    1    217-220   TFED
    2    336-339   TKYE

---

[5] PDOC00008 PS00008 MYRISTYL
N-myristoylation site

Number of matches: 10
    1      2-7     GSPGAT
    2      5-10    GATTGW
    3     45-50    GVSVTQ
    4    113-118   GGTHSH
    5    119-124   GVKTGQ
    6    130-135   GTHRTC
    7    146-151   GVVPSR
    8    225-230   GGSVGI
    9    297-302   GLIPTA
   10    306-311   GTGAAW

---

[6] PDOC00932 PS01212 P2X_RECEPTOR
ATP P2X receptors signature 225-251   GGSVGIRVHWDCDLDTGDSGCWPHYSF Membrane spanning structure and domains:

| Helix | Begin | End | Score | Certainty |
|---|---|---|---|---|
| 1 | 69 | 89 | 0.782 | Putative |
| 2 | 299 | 319 | 1.835 | Certain |

BLAST Alignment to Top Hit:
>CRA|18000005098398 /altid=gi|4885535 /def=ref|NP_005437.1|
        purinergic receptor P2X-like 1, orphan receptor; P2X
        specifically expressed in skeletal muscle; purinoceptor
        P2X6 [Homo sapiens] /org=Homo sapiens /taxon=9606

FIGURE 2A

```
        /dataset=nraa /length=431
     Length = 431
 Score =  857 bits (2189), Expect = 0.0
 Identities = 405/431 (93%), Positives = 405/431 (93%), Gaps = 26/431 (6%)

Query: 1    MGSPGATTGWGLLDYKTEK------------------------WALLAKKGYQERDLE 34
            MGSPGATTGWGLLDYKTEK                        WALLAKKGYQERDLE
Sbjct: 1    MGSPGATTGWGLLDYKTEKYVMTRNWRVGALQRLLQFGIVVYVVGWALLAKKGYQERDLE 60

Query: 35   PQFSIITKLKGVSVTQIKELGNRLWDVADFVKPPQGENVFFLVTNFLVTPAQVQGRCPEH 94
            PQFSIITKLKGVSVTQIKELGNRLWDVADFVKPPQGENVFFLVTNFLVTPAQVQGRCPEH
Sbjct: 61   PQFSIITKLKGVSVTQIKELGNRLWDVADFVKPPQGENVFFLVTNFLVTPAQVQGRCPEH 120

Query: 95   PSVPLANCWVDEDCPEGEGGTHSHGVKTGQCVVFNGTHRTCEIWSWCPVESGVVPSRPLL 154
            PSVPLANCWVDEDCPEGEGGTHSHGVKTGQCVVFNGTHRTCEIWSWCPVESGVVPSRPLL
Sbjct: 121  PSVPLANCWVDEDCPEGEGGTHSHGVKTGQCVVFNGTHRTCEIWSWCPVESGVVPSRPLL 180

Query: 155  AQAQNFTLFIKNTVTFSKFNFSKSNALETWDPTYFKHCRYEPQFSPYCPVFRIGDLVAKA 214
            AQAQNFTLFIKNTVTFSKFNFSKSNALETWDPTYFKHCRYEPQFSPYCPVFRIGDLVAKA
Sbjct: 181  AQAQNFTLFIKNTVTFSKFNFSKSNALETWDPTYFKHCRYEPQFSPYCPVFRIGDLVAKA 240

Query: 215  GGTFEDLALLGGSVGIRVHWDCDLDTGDSGCWPHYSFQLQEKSYNFRTATHWWEQPGVEA 274
            GGTFEDLALLGGSVGIRVHWDCDLDTGDSGCWPHYSFQLQEKSYNFRTATHWWEQPGVEA
Sbjct: 241  GGTFEDLALLGGSVGIRVHWDCDLDTGDSGCWPHYSFQLQEKSYNFRTATHWWEQPGVEA 300

Query: 275  RTLLKLYGIRFDILVTGQAGKFGLIPTAVTLGTGAAWLGVVTFFCDLLLLYVDREAHFYW 334
            RTLLKLYGIRFDILVTGQAGKFGLIPTAVTLGTGAAWLGVVTFFCDLLLLYVDREAHFYW
Sbjct: 301  RTLLKLYGIRFDILVTGQAGKFGLIPTAVTLGTGAAWLGVVTFFCDLLLLYVDREAHFYW 360

Query: 335  RTKYEEAKAPKATANSVWRELALASQARLAECLRRSSAPAPTATAAGSQTQTPGWPCPSS 394
            RTKYEEAKAPKATANSVWRELALASQARLAECLRRSSAPAPTATAAGSQTQTPGWPCPSS
Sbjct: 361  RTKYEEAKAPKATANSVWRELALASQARLAECLRRSSAPAPTATAAGSQTQTPGWPCPSS 420

Query: 395  DTHLPTHSGSL 405
            DTHLPTHSGSL
Sbjct: 421  DTHLPTHSGSL 431 (SEQ ID NO: 4)
```

Hmmer search results (Pfam):
Scores for sequence family classification (score includes all domains):

| Model | Description | Score | E-value | N |
|---|---|---|---|---|
| CE00369 | E00369 P2X6_receptor | 1180.5 | 0 | 2 |
| PF00864 | ATP P2X receptor | 870.0 | 7.4e-258 | 1 |
| CE00207 | CE00207 PURINERGIC | 366.8 | 5.9e-111 | 1 |
| CE00370 | E00370 P2X4_receptor | 336.8 | 1.9e-109 | 1 |
| CE00368 | E00368 P2X7_receptor | 124.1 | 6.5e-36 | 1 |
| PF00095 | WAP-type (Whey Acidic Protein) 'four-disulfi | 8.7 | 1.1 | 1 |
| PF01841 | Transglutaminase-like superfamily | 6.0 | 6.3 | 1 |
| PF01368 | DHH family | 2.5 | 6.8 | 1 |

Parsed for domains:

| Model | Domain | seq-f | seq-t | hmm-f | hmm-t | score | E-value |
|---|---|---|---|---|---|---|---|
| CE00369 | 1/2 | 1 | 19 [. | 1 | 21 [. | 36.3 | 2.1e-11 |
| PF00095 | 1/1 | 87 | 111 .. | 1 | 40 [. | 8.7 | 1.1 |
| PF01841 | 1/1 | 120 | 130 .. | 1 | 11 [. | 6.0 | 6.3 |
| PF01368 | 1/1 | 221 | 237 .. | 1 | 19 [. | 2.5 | 6.8 |
| CE00368 | 1/1 | 54 | 299 .. | 85 | 333 .. | 124.1 | 6.5e-36 |
| CE00370 | 1/1 | 20 | 338 .. | 46 | 372 .. | 336.8 | 1.9e-109 |
| CE00207 | 1/1 | 20 | 345 .. | 47 | 393 .. | 366.8 | 5.9e-111 |
| CE00369 | 2/2 | 20 | 351 .. | 48 | 379 .] | 1143.5 | 0 |
| PF00864 | 1/1 | 20 | 354 .. | 34 | 395 .] | 870.0 | 7.4e-258 |

FIGURE 2B

```
   1 TCTCCAAGTC CATGGGTGCC TGGTAGGAGA CAGGGGGATG AATGTGAACC
  51 CCTGCATGGC TATAGCCACC TGCCTCCTCC CCTGCCCTGC ATCACTACCT
 101 GGCCTATTTT TTGCCTCTAG AAGCACTGCT TCCTATGCTC CTTAGGACCA
 151 CTGCCCGCAT ATGACAGATA AGAACATCGA GGCTAAGGCA ACGCAAATCT
 201 TTTCCTTAAA GTCATACAGC TGTCAAAAGA AAGCTGGACA ACCTGGGCAA
 251 CATAGCGAGA TAAAAAATTA TTTAAATTAG CCAGATGTGG TAGCCCCCTG
 301 TAGTCTCAGC GACTCAGGAG GCTGAGGCAG GAGGCTCACC AGAGTGCAGA
 351 GTTCAAGGAT GCAGTGAGCT ATGATCCTGC CACTGCACTG AAAGCTGGGT
 401 GACAGAGCAA GACCCTGGCT CTAATAAATG AATACATAAA GTCTCACAGC
 451 TAGTGGTAGC TAATCCTGCC AGAGTCAGGC CTCTACCTGT CTGATGACAA
 501 ATGGCACACT ATGTCTTTTA ACCTGATTGC AGACCACAAA TGTTTTGTGA
 551 ATATTTTCCC CAGGGAAAAA ACCGGAAGTA GTTCTAAATT CTATACATCC
 601 ATTATATTAG TTTTACCTGT GGATTGGGAA AACCCAGCTC TGATTGCATT
 651 TCAGGGCGGG ACAGCCTTTG GTGCCATTGT TGGCGGGATT TTCCATTTTA
 701 ACCTCCTTCT AGAAGCGCCT TCTCATGGTA AAGTTCCTGA TGCCGCCAGG
 751 AGCGCCGAGG AGAGGGCAGG GGGCTGGAGA CGCCCCGCAG AGGGCTACGT
 801 GCCCTGCTGG ACAGAGGTCT CCTGCCTCCT CGGCGGCGCC AGCCCACCTC
 851 CCACAACCCC TGCGGGAGAA GCCCCAAGG GGAGGAGACG GGCCTGGCCC
 901 CTGCCCCGAG CACCTTCCGT CTCTAGGTCG GAGTCTGAAT CGGCCTTGGG
 951 ACCCTGCTTG GCTTCGGGGA CCCCTGCAAG ACGTCCACAG GCCGCCGTCG
1001 CCTCTTCCTC CTGCTTTTTA TCCTCCCCAG ACCTCTGGCA GGAACCGCTC
1051 ATCGTTACGC CCCTTTCGCA GCCTCAGACC CTGAGGCGGA GACCGCTTGG
1101 CGCCTCACTT AGAGCGCGAC CCGGGGATGT GGGCGGAGTC TGCGGCTGCG
1151 CTGACCAATC GAGTGTGGCG TCCATCGACT GGCGTCTGCC ACGGCAATTA
1201 GCGACGCGCT CCCCCGCGGC GGTCGCCCCG GCAACCCAGT GCTGTAGGTT
1251 GCCGTAGAAA CCGTGGCTCT CCTGCGCTGA GGCTCCTCGC CTGAGAGGAT
1301 AAACTGCACG CGCCACGGGC TATGCACTGG GCTGGGCGCC TTGTGGGCAT
1351 CCTCCCTGCC TTCCTAGGGG GTTCCAGCAT CGCCCCCCTT TCGTGGACTG
1401 GGAAACACGC CTGACTCCAG GACTTGTGTT GTCCTCACTG CACTGGGGAA
1451 GGTGGCGGGG GCAGCTTTTC AGGAGGGCCT GGGGAACTTC GCAGAGCCAG
1501 GTCACCCTCT CACTCTGTGC CTCTTAGTTA TCTTGCATGC TCTGGTCTTT
1551 GCATACGCTG CTCCCTGCAC CAGGAACCTC CATCCCCATC TTTGTCTGCT
1601 TGTCGAACTT CAGAAATCTG CAAGGGTCAG CTTAGAGGTC ACTTCTTCCG
1651 GAAGCTTTCC TCAACACCCT CCCCGCCCTG CTGCTGCTGC CCTCAGGCCC
1701 TCCTCTCACA GCACTGATAA CAGCTGTCCG TCTCCACCCT CCCACCACCT
1751 CCACTCCCAC CCCAGGAAGT GAGGCCAGAG GGCAGGGACA GAGCTGCTGC
1801 TGTTCTCTGT GTGCCAGGGC CCAGCAAAGG GAATGTAGGG AGGGTGGGAG
1851 GTGCAGGGCA GCTGGGATTA GGGGTTGAGG GCTGGGTGTT GGAGGCTGGA
1901 TCTGGATCCT GCTTTAGTGG AAGTGTCCCT TTAACAGCAA CTGGCCTGGC
1951 CTGGCTCGGG CCCTGCTTTG CCTCCTGTTC AGCTGCGGCT GCAGCTGCCA
2001 TGCTGACTCA TGTGCCCGCA GCTAGCAGGA GCTGGCAGCA TGGGCTCCCC
2051 AGGGGCTACG ACAGGCTGGG GGCTTCTGGA TTATAAGACG GAGAAGTATG
2101 TGATGACCAG GAACTGGCGG GTGGGCGCCC TGCAGAGGCT GCTGCAGTTT
2151 GGGATCGTGG TCTATGTGGT AGGGTAAGAG AGAAGAGCTT TTGGCCAGGC
2201 TGGAGGGGCA AGGGAAGAGG TGGGGGGTGG GCTTGGTCC TGCTGGGTTG
2251 AAGTTGAGGG TTGGGCTGTT TAGGGGCTGG AGTGGAAGGG GGCAGATTGG
2301 GACGGGGTTG GGGAGAGCTA GGCGATACAA GACAGGAGAG CAAGAACAAG
2351 CTGTGTGTTT GTCCTGTGTG TCCACTTGCC TCCTTCCCAG GCCCCCACCC
2401 AGGCCCCACC CAGGGGGCAC ATGACATAGT CCTTAACATC TGTGAGAGCT
2451 GGAGCACTAG GCCCCAGAG AGACCACCAG CTGTATCTCG GGTCAGGAGA
2501 GTCTGTAAGG GGGAAGCTGG ATCTAGTCAG GCTGGGGGTG GGTGCTGGCT
2551 AGTGAAGGTG ATTGTCTGAG GCATTGGCT CTCTGATGCA TGGCTGGAGC
2601 TTCTGTCTCA TTCAGGGGGT CTGGAGTGGG AAGTGGGGCC AGAGAGGAGG
2651 TGGGGCCTTC GATGTTGGGC CGGGAGCCTG TAGGGTGTGG GGGGAGAACT
2701 GAGCATGTAG GGCTCAGCTC CGCCCCTGTC ACTACACGCT GGGGACACAC
2751 CACACTGCCC GACTTCTCCT CCCCAGGTGG GCTCTCCTCG CCAAAAAAGG
2801 CTACCAGGAG CGGGACCTGG AACCCAGTT TTCCATCATC ACCAAACTCA
2851 AAGGGGTTTC CGTCACTCAG ATCAAGGAGC TTGGAAACCG GCTGTGGGAT
2901 GTGGCCGACT TCGTGAAGCC ACCTCAGGTG GGGGCCCTGA TGTTGCTGAC
2951 GGGGGCGCAA GTCCTTTCCC CACTGACAGC CTGAACACCC GCCATGCAGC
3001 CAGTGTGTGC GAGAGAGAAG CATGTGATGC CAGAGACGGC TGCGGGTTCT
3051 CAGGAAGGGC TTCACAGAGG AGTGGCACCT GGACAGGACT TTCAGGGATG
3101 TGTAGGAGGT TTTGGGGTGG AAAAAGGGGC CACTCAAGAA GCCAGGCCAG
3151 GGTTGGACGT GCTGGCTCAC GCCTGTAATC CCAGCACTTT GGGAGGCCGA
3201 GGCAGGTGGA TCACGAGATT GAGAGTATCC TGGCTAACAC GGTGAAACCC
3251 CATCTCTATT AAAAATACAA AAAATTAGCC GGGCATGGTG GTGGGCGCCT
3301 GTAGTCCCAG CTACTCGGGA GGCTGGGGCA GGAGAATGGC ATGAACCCGG
3351 GAGGTGGAGC TTGCAGTGAG CCGAGATTGC ACCACTGCAC TCCAGCCTGG
3401 GTGGCAAAGC GAGACTCTGT CTCAAAAAAA AAAAAAAAA GCCAGGCCAG
3451 AGAAACTGCA TTTCCAAAGA CTGCCAACAG AAAAGAAGGG AGTGTCCAGG
```

FIGURE 3A

```
3501 ACTAATGGCT TGAGCTTGAG AGTGGTGTGA GGTGCTGGGG CATGGAACTT
3551 CCCTGTAGCC CTGCTCCCTG ACCTGGGGCA CTACGGTCAG GTGCTGCTCC
3601 TCCCCTCTTC TCGGCTGCGT TTTCCTCCTC CCTCCACCCA GCTCATCCCC
3651 AGCCTCAACT GCCACTTCTG CTCCTCTGAT GCCCAGGGTG TATTCCCAGT
3701 GATCACCTGC CCAGAGCACA GCTGTCTTCT AGGTGCACAC CCACATGTCC
3751 AAAGATCAAT TATTTTCCTC TCCTGGCATG GCCTCTGTGA CGCCCACTAG
3801 TCATGGTGGC TGTGACATCC ACTAGTGCCT CAGCCAGACC CGTGACTCAC
3851 CCTGGACCCC TTCCTGTCCC TTCCAAGATT TTTCACCACT ACCCATGCCA
3901 TGCCATGCAT GAGACTATGG CCTCCTAGAG GGTCCCTAGA TGCCCCTCTC
3951 GCCTCCTCCC TTACTGCTCG GTGCACACCA CGCAGCAGCC AAGCTGAACT
4001 TTCACACCAG GCATCATGAG AGCCTGCAGC GCCTGCTTCT ACCCTCAGGA
4051 ATTCCCCCAA CCCTGCCCAT GACGGTGTCC ACACTTTCCT CCCAATCCTA
4101 ATGGCTGCCA CTCCCAGCAC CATCTGGCCA GCCCTCACCT TCCCTTCCTG
4151 GGCATACATT CCCCAAATTC ACAGTGCTCT CACGAGCAGC ACTGGAGGGT
4201 CAGCCTTTCT TTCCAATGTC CTCGGCCACC CGTTGACCAC AGACACAGCT
4251 TTCCCTCTTC TCCCTTGGCC CCTGCCATGC CAGTGCTGCT GTGTGTGAGA
4301 TGGGAGACTC ACCTCGTCTC CATCCTGAGC AGGTGCTGGG CCCAGCTCTC
4351 CCTTGGATCT TCAGTACTAG AAGCAGCAGG CTGTTGGAAT ATTCTGGTTG
4401 GAGCCAGGCA TGGTAGCTGG AGCCTGTAGT CCCAGCTACT TGGGAGGCTG
4451 AGGCAGGAGG ACCTCTTGAG TCCAGGAGTT AGAGGTTGCA GTGAGCACTG
4501 ATCACAACAC TACACTCCAG CCTGGGTGAC GAAGTGTAAT CCTGTCTCTA
4551 AATACACACA TACACATGCA CACACACACA CAAATTTTGG TTGAGACAAG
4601 AGACTTGTCT CAAGAGATGG ACATGGGCAC AAGGCTTCCT GGTCTCAAAA
4651 ATGGCCAGAA CCACTGCCAG CCTCCCATCT CTGCTTCAGT CTGCCTTACA
4701 GGGGGACAGG GTTAATGACT TGATGGGGCC AACATCCCTT CCCTCATAAA
4751 CCAGGCTGCC GGCTTCCGGC CTTTCCAGTC AACACGAGCC CAGCCAGGCC
4801 AACCTTGAGA CTTGCCTCCT AGGGAGAGAA CGTGTTCTTC TTGGTGACCA
4851 ACTTCCTTGT GACGCCAGCC CAAGTTCAGG GCAGATGCCC AGAGGTGAGT
4901 TTACCCAGGA TCCTCCCAGC GGGTCCCTTG TTCCTCCATC AGCCCCAGGT
4951 GGCCACCCGT GTTTCCCTTT CCCCTTCCCA GGTGGCTGAA GGCTCAGCCT
5001 GTGCTCGGTG TCCCCCAGGC ACTGGGCTAC ATCTTTTCCT GAATCATTAT
5051 GTTCAGTCTT CACATATCCC CTGCCTGGTA GGAAGTCCTG TGATCCCCAT
5101 TTCAGAGGAG AAGACTGAGG CTCAGTGAGG TTGAGTCACT TTCTTAAGGC
5151 CTCCAGGCCT GTGGGTGACA GGACCCCGAG CTCTGGGCAG CAGCAGTTCC
5201 CATGAGGTGT CCAGGCCCTC CCATCCTGGT CCTGCCTCTG GGTACTCTCC
5251 AGGTTGGTAG TGTGACACCC AGAGGTTCTA ACATGCTCAG GGAGGTTCTA
5301 ATAGCAAGAG CCAAGCTGGA ATATCACCTC CCCTTGTCTG TGCCCAGCCT
5351 CTATTAATAT GTCCTGAGGC AGCTTTCATC TTTGTGGGCC AACACAGCAC
5401 ACTCTTGCTC ATGGTGAATT CAGGATTGCT TATGATTTCT GGATAGTTTT
5451 TTTTGTTTTA TTTTTGAGAC GGAGTTTCAC TCTGTCACCC ACGCTGGAGT
5501 GCAGTGGCAG ATATCAGCTC ACTGCAAGCT CTGCCTCTCA GGTTCAGGCA
5551 ATTCTCCTGC CTCAGCCTCC GGAGTAGCTG GTACTACAGG CGCCTGCCAC
5601 CACGCCCAGC TAATTTTTTT TTTTTTTGT ATTTTAGTG GAGACGGGGT
5651 TTCACGGTGT TAGCCAGGAT GGTCTCCATC TCCTGACCTC ATGATCCACC
5701 TGCCTCGGCC TCCCAAAGTG CTGGGATTAC AGGCGTGAGC CACCACGCCC
5751 GGCCTGATTT CTGGATAGTT TTTACATCAA CCGTGGTCAA GCCAGATGCC
5801 CCCACCTTGT TCTTCTTCAT TTCTGATCCA GAAATGCTGA TTCTCCCCCT
5851 GACATTTCAC CTTTTCCCCT TGCCTGGGGA TGTCCCTGGG ATCCTGCATC
5901 TGTCACAGAG CATGCTCATT CTCTCCAGCT GTGAATTTTG TTTGAACTAT
5951 TGGGACTCAG GACATAGTCC TGAAAGTTTA CCTCCACAGT GACATCTTTA
6001 GGCAAGTCCA ACATTTACGT GCCTCCTGGG CTGGAGGGTC GTTGTGCAGA
6051 CAGCTGTCCC CTGAGCCCTG GTGGCTGGTC CTAGCACAGT TGCTGGAGAC
6101 ATCCCATGTC CGTAGTTGGA AATATGCACA AAGGATTGCT TACTCTTTTT
6151 GTTTGTTTGT TTTTTTGAGA TGGAGTCTTG CTCTTGTCCC AAGGCTGGA
6201 GTTCAATGGC ACGATCTCGG CTCACTGCAA CCTCCGCCTC CTGGGTTCAA
6251 GCAGTTCTCC TGCTCACCCC CTGAGTAGCT GGGATTACAG GTGCCCGCA
6301 CTGTGCCCAG CTAATTTTTG TATTTTAAGT AGAGACGGGG TTTCACCATG
6351 TTGGCCAGGC TGGTCTCGAA CTCCTGGCCT CAGGTGACCC ACCAGCCTCG
6401 GCCTCTCAAA GTGCTGGGAT TACAGGCGTG AGCCTGCCGA GAGCTTGGTC
6451 GGGGAGACCT GAACCCAGCG GTGCTAAAGG AATTAAAGAC AAACACACAT
6501 AAATATAGAG GTGTGGAGTG GGAAATCAGG GGTATCACAG CCTTCAGAGC
6551 TGACAGCCTC GAACAGATTT ACCCACATAT TTATTGACAG CAAGCCAGTG
6601 ATAAGCATTG TTTCTACCAG ATTATAGATT AACTAAAAGT ATTCCTTATG
6651 GGAAACAAAG GGATGGGCTC TGGTTGGTTA TCTGCAGCAG GAGCATGTCC
6701 TTAAATCACA GATCGCTCAT GCTATTGTTT GTGGTTTAAG AACGCCTTTA
6751 AGCGGTTTTC CGCCCTGGGT GGGCCAGGTT TTCCTTGCCC TCATTCCGGT
6801 AAACCCACAA ACTTCCAGTG TGGGTGTCGT GGCTATCACA AACATGTCAG
6851 AGTGCTGCAG AGATTTTGTT TATGCCAGA TTTTGGGGGC CTCTTCCCAA
6901 CATGAGCCAC TGTGCCTGGC AGGATGTGCT TACTCTTGGT GAACCCACAC
6951 AATGTCCTTC TCTTTCTTAA TGCTCAGATG TGCATTTAGT GTTCAGTTTG
```

FIGURE 3B

```
7001 TAGACCGTTC TGAAATTTGG CTGGATCTGT GGGTCTGTGT TTTTCAGAAT
7051 CTGTGCAATT CCTCTTTGTC TGCAACCACA CTTCTGGCTC TTCCCATGAA
7101 ACGTCAGGGC TGGGTCGTAA TTATCAGATC TGACAACCTG GCTTTCCCGG
7151 AAGACCAGAG TTCTGCCAGC TCCTCTAGGG ATCCTGGTGC CTGATCCCTC
7201 CCTTACATGC ACCATGCTCT TTATAGTGTC ACCTCCCTCA GCAGACACCG
7251 CTGAGCCTCC CCGCTGGGCC AGGGGGCTAG CTAGGCTAAA TTCACAAAAC
7301 TCCATCTCCC ATACTTCAAA GACCACCCAC ATGGACAGCC CAGCCCAGGT
7351 GGCAGGTCCG ATGATGGGAC AGAGGCTGTA GGTGGGGGAC CTAGGGCTGC
7401 ACTTGAGCAG AATCTTTTTT TTTTTTTCT TTTTTTTTTT TTTGAGACAG
7451 AGTCTCGCTC TGTCACCCAG GCTGGAGTGC AGTGGCGTGA TCTCGGCTCA
7501 CTGCACACCT CCACCTCCTT GGTTCAAGCG ATTCTCCTGC CTCAGCCTCC
7551 CAAGTAGGTG GGACTACAGG CACACACCAC CACACTCGGC TAATTTTTGT
7601 ATTTTTAATA GAGACAGGGT TTTGCTGTGT CGGCCAGGCT GGTCTCGAAC
7651 TCCTGACCTC AGGTAATCCG CCCACCTTGG CTTCTCAAAG TGTTGGGATT
7701 ACAGGTGTGC CAGGCCAAGC AGAATCTTAA AAAAAGGTGG GGAGAAGCTG
7751 GTGAGCAGGT GGATTTGGTT GAAGCAGGAT GTCGACACAG AGGGGGCTTG
7801 GTGGGTAAAG GCCCTGAGCT GTGTGAGGTG AGGTGCCTTT AGGGCTACCT
7851 GCCACTGGGT GGAGCTGAAG TGAAGATTTG GACTGGGGTG GGAAGAAGGT
7901 AGTTCAGGAT TTCAGGGGCC CCTGTAAGCC CCACTAAGGA GCTAAACTGT
7951 TTTTGTTTGT TTGTTTTCTT TTTCTCTTTT CTTTTTTTTC CTGTAGCAAT
8001 GAGGTCTTGC TTTGTTGCCC AGGCTGGTCT CGAACTCCTG AGCTCAGGCA
8051 ATCCGCCTAC TTTGGACTCT CAAAGTGCTA GGATTACAGG CGTGAGCCAC
8101 TGTGCCTGGC AGGAGCTAAA CTTGATTAGA GGAACAGAAG AGAGCCACAC
8151 GTGGGCTCAG AGGCAGGGTG CTCAGTTTCC TGCACATTGG GATGCACCAC
8201 TTGGGCTGCT GGGCATAGGT GGATGAGGGT ATGGGAAGAC GTGGGGGCCC
8251 CACTGGTGGT CACTGTGGGG TCTAGTTGGA GGAGACGGTA GCCCAGCTGG
8301 GGTGAAGAGG AGAGGCAGAC ACAGGACATA GGTAGGGACA AAGAAGCAGA
8351 GCATGTGGCT CTGCTCCGAC CTCCACCCAA TCACGACGGC CCTGTCTTTC
8401 AGAAAGTCCC ACCGCCTCAT TCTGGCTTCT CAGAGGCCCT CAGCCTTCCT
8451 TGCGCCCCTG GTGCTGGTGT TCTTCCTGCT GCCCCTGAGC TGAGTGCCCT
8501 GGGCAGCAGT GTCCATCCTC AGTTGGGGCA GGACCATGCC TGGGAGAGTG
8551 CCCGATGCTC AAGGGTGCCT TCGTCTCTGG GGTCTGGGAC CCCAGAAAGC
8601 TCACCTGTCC TCCCCTTCTG CCAGAGCCCC ATAGTCCCAT GCCTCTGTGC
8651 AGGCATTAAT GTCCCCAGGT TACAGAAGAG CGAGCAGGAA GGAGTAGCCT
8701 GTGGTCCCTC AGCAAGGGTG TGGGGTCCTG CTTCAATACC CAAGCCCCTG
8751 ACTCTAGGGC CCTGATCTTT GTCAGCTATG TCCCCATGCC GGGCATCAAA
8801 AACTCACCCT CCCAAGGTAT CTTCACCTTC CCTGATCTGT CATCCAAATT
8851 GGACCAGAGG AGCTAGACCT GGAAGAATCA CTTCCGCATC CACCAGGGAC
8901 AGAACTGTCA GGAGGGAAGG GGCAGGGTGC GTTGTCTCAC GCCTGTAATC
8951 CCAGCACTCT GGGAGGCTGA GACAGGAGTTA TTGCTTGAGG CCAGGAGTTA
9001 AAAACCAGCC TGGTCAACAT AGCAAGACTC CATCTCTACA AAAAAAAAAT
9051 ATTAAAAAAT CAGCCAGGCA CAGTGGTGTG TGTCTGTAGT CCCAGCTACT
9101 GGGAATACTG AGGTGAGAGG ATTGCTTAAG CCCGGGAGGG CGAGGCTGTA
9151 GTGAGCCATG ATCATACCAC TGCACTAGAG CCTGGACAAC AGAGTGAGAC
9201 CGAATCACTA AAAATAAATT TTTTGAAAAA GGAGGAAAGG GGTCTCCCTT
9251 TGTCTTTGAA ATACAGTACT GTACCTTCAT CTGGCCAGGG CATTGCTCCG
9301 CTCCCTCCTC TGACCACCTC CTTTTATTTG CACCCTCCAG CTTTCCTCGTG
9351 TGGCCCCACA CTCAGGGTAC TCTGGCGGCG GGTGGTGAG GTTGTTTAAG
9401 GTGGGAAGGG GGCCTGTCCT TCCCACCTTG AACCTCCCTG CCTTTGAGAC
9451 TGGGCTGTGG AGGGGAGACA TCCCCTGTGC CATTGGTGAC TGCTCTCTCT
9501 CCCACCTCAG CACCCGTCCG TCCCGACGGG GTCGACGAGG
9551 ACTGCCCCGA AGGGGAGGGA GGCACACACA GCCACGGTAA CTGTGGGCTC
9601 TGTCTTCCAG TGCCCCTAGC AGGGTGGGGG CCGGGCTGGG ATCCTGGGTG
9651 GCTCCTGAGT GCAGGCCCTG CTCGCCTCTG TCCCTGCATC TCTCTTTCTG
9701 CCAACAACCC CCTGGCTGAA GGCCTCCCCA GGCCTGCAGA GATTTGAAGG
9751 TCTGGAGTTC ATCTTTTGTT TTCTAGGTGT AAAAACAGGC CAGTGTGTGG
9801 TGTTCAATGG GACCCACAGG ACCTGTGAGA TCTGGAGTTG GTGCCCCGTG
9851 GAGAGTGGCG TTGTGCCCTC GTAAGTGTCC CCACAATCCC CTACCCCAAC
9901 TGGCGCAGGG CCCCAGGCCT GGCAGAGGCT GTCACCTCCC TTCCACCTGC
9951 AGGAGGCCCC TGCTGGCCCA GGCCCAGAAC TTCACACTGT TCATCAAAAA
10001 CACAGTCACC TTCAGCAAGT TCAACTTCTC TAAGTAAGCA GAGTGGGTCT
10051 CATCTGCCCC AAGACCCTCC TTGTCCCCTA CCTCATCTGA CCTTTCCCAC
10101 TCCTCCCAGG TCCAATGCCT TGGAGACCTG GACCCCACC TATTTTAAGC
10151 ACTGCCGCTA TGAACCACAA TTCAGCCCCT ACTGTCCCGT GTTCCGCATT
10201 GGGGACCTCG TGGCCAAGGC TGGAGGGACC TTCGAGGACC TGGCGTTGCT
10251 GGTGGGTCCC AAGTTGGGGG CAGGGTTCCT AGAGGGCTCT GGGAGAGGGT
10301 CCCGGGCCCA CCCACCGGTG GAAAAGCTAT GTGCTATGTG CAGGGTGGCT
10351 CTGTAGGCAT CAGAGTTCAC TGGGATTGTG ACCTGGACAC CGGGGACTCT
10401 GGCTGCTGGC CTCACTACTC CTTCCAGCTG CAGGAGAAGA GCTACAACTT
10451 CAGGTGAGGC CCCACTGCTC CCAGTGCCCA GCTGCTGGGC CCATCGCCCT
```

FIGURE 3C

```
10501 CTCACTGTGG CGGCCAGGAC AGACCACACC CAGGCCCAGG CCTCTAGATA
10551 TTCCACTACG TGTGCAAGGG GGTCCCAGGA GCAGGAGAGA GCTGTTCTCA
10601 ACCCCACATC CTCCAGCACA GGCTCCGTCC TGCTGCCCCA AGTCCTGAGC
10651 CCTCCACCCC ATCTGTCCCA GGCCCCTGCC CAGCTCAGGC TCCTCACTGC
10701 CAGCCCTTCC TCCACCCCAC CTCGCTTCTA GTATCTCCCC TCCACAGCAA
10751 TGGGGTGTTT CATTTTTACT TTCCCCTTCT CCCCTTCAGC TTTGTTTTTT
10801 TTTTTTTAAG ACAGAATCTC ATTCTGTCAC CCAGGCTGGA GTGCAGTGGC
10851 CCGACCTCGG CTCACTGTAA CCTCTGCTTC CTGGGTTCAA CCGATTCTCC
10901 TTCCTCAGCC TCCTGAGTAG CTGGAATTAC AGGTGCTCGC CACTACTCCC
10951 AGCTAATTTT TATATTTTGG TAGATAGAGA TGGGTTTTCA CAATGTTGGC
11001 CAGGCTGGTC TCAAACCCCT GACCTCAGGT GATCCACCCA CCTCAGCCTC
11051 CCGAAGGGCT AGGATTACAG ACGTAAACCA CCATGTCTGG CCTCCCTTCC
11101 GCTTTTACCT AAACTTTTTT TTTTTTTTTG AGATGGAGTC TCACTCTGTC
11151 GCCCAGGCTG GAGTACAGTG GCGGGATCTC AGCTCACTGC AAGTTCCGCT
11201 TCCCGTGTTC ACGCCATTCT CCTGCCTCAG CCTCCCAAGT AGCTGGGACT
11251 ACGGGTGCAC GCCTCCACGC CCGGCTAATT TTTGCATTTT TAGTAGAGAC
11301 AGGGTTTCAC CATGTTGGCC AGGATGGTCT CGATCTCTTG ACCTCGTGAT
11351 CCACCTGCCT CAGCCTCCCA TAGTGCTGGG ATTACAGGCG TGAGCCACCA
11401 CGCCCGACCT TTTTTTTTGA AACGGAGTTT TCACTTTCTT GTAGTCCAGG
11451 CTGGAATGCA ATGGCGTGGT CTTGGCTCAC TGCAACCTCT GCCTCCTGGG
11501 TTCAGGTGAT TTTCAGCCT CTGCCTCCAG AGTAGCTGGG ATGACAGGTG
11551 TGCACCACCA CACCCAACTA ATTTTTGTAT TTTTAGTAGA GATGGTGTTT
11601 TGCCATGTTG GCCAGGCTGG TCTCGAACTT CTGACCTCAG GTGATCTGCC
11651 CACTTCAGCC TCCCAAAGTG CTGGGATTAC AGGCATGAGC CACCAAGCCT
11701 GTTTTTTTTG TGTTTTTTTT TTTTTTTTTT TTAGATGAAG TTTTGCTCTT
11751 GTTGCCCAGA CTGGAGTGCA GTGGCCCGAT CTCGGCTCAC TGCAATCTTT
11801 GCCTCTCGGG TTCAAGCAAT TCTCCTGCCT CAGCCTCCTG AGTAGCTGTG
11851 ATTACAGGTG CACACCACCA CACCCAGCTA ATTTTTGTGT TTTTACTAGA
11901 GATGGGGTTT CACCATATTG GTCAGGCTGG TCTCGAACTC CTGACCTCAG
11951 GTGATCCACC TGCCTCAGCC TCCCAAAGTG CTGGGATTAC AGGTGTGAGC
12001 CACTGTGCCT GGCCTCAAGT TTCATAAATT GCATTTATTA TCATGTCTTT
12051 GAGTCTTCTA AGCAGATCTA TTGGATCCTT CTGCCACCGA GCGTCACCTC
12101 GTCATGCAGG CAGGCACACA CGACCACCAG GCCTGGGGAT GATGCCCCTC
12151 AACATAGCTC ACTGCACCCC GTCTGATCTG GCTTCCCCAA CCTCCCCAGC
12201 CCTTCGAAAC CACGTGGGGC TGGCTCCCAC CCACATCCTG TTCCCCTGAC
12251 CTCTGTGCTG GCAAACCACC TGTGTGCATG TTCCTTCAGG CCCAGCCTCA
12301 TGTCCCCTCC AGGAAGTCTA CCCCAGTTCC CAGGGAAGAG TGAGTTCCCA
12351 TCTCTGGAAT CCCTCAGCCC TGAGCCTGCC CCTTCACATC CCCCGCTGCT
12401 GGGTCTGTTT AGGGACTCCT CTGTCCCCCG TCCTCTCAGC AGGCAGGGAA
12451 CTTCTGAGGG ACAGGTCTTC GTTTGCTTTT TCTGTTTTCT CACCAATTAC
12501 ATAGGGCTGA GACCCAGGAC TCAGGCTTGG GCTGGGGGTT TATAGAGTCA
12551 ATTGACAAGT TGGACAGAGG TCTGGCAGGG CCAGCCCCAC CTGGGGGTGG
12601 GCAAAGCAGG TCACCAGAGC CTTCTTTCCT GCCCACAGGA CAGCCACTCA
12651 CTGGTGGGAG CAACCGGGTG TGGAGGCCCG CACCCTGCTC AAGCTCTATG
12701 GAATCCGCTT CGACATCCTC GTCACCGGGC AGGTAGGCAC AGGTAGGGGT
12751 CAGGCCGGGG ATGGGATGGG GCAGGCAGAC AGGGCTGGAG GAGGCATGAG
12801 GCTGACAGTC GTGGGCTGAG AGGTTCAGCT CAGATCTCTC TCAGGCAGGG
12851 AAGTTCGGGC TCATCCCCAC GGCCGTCACA CTGGGCACCG GGGCAGCTTG
12901 GCTGGGCGTG GTGAGTGCGA GCACTGTGGG CACCTGCAGG CTGCAGTGAG
12951 TGCTGCTGAC CAGGGTGTGT CCAATGCATG CTGGAGCCTC CGGTGCCTGC
13001 ACATTGAGTC TCGGGGTGCA GGCTGGGGAG GTGGCAGGGA AGCAGGCTCG
13051 GGGGCTGGAA CATGGGTTGG CCCTGCCTCT CCCAGGTCAC CTTTTTCTGT
13101 GACCTGCTAC TGCTGTATGT GGATAGAGAA GCCCATTTCT ACTGGAGGAC
13151 AAAGTATGAG GAGGTGAGCT GAGGTCGCTC TGCTTGGACC CTGGGTTCTG
13201 CCACACTTAG GAAGATGTTG GCTGGATCCC TGACCTGCTG TCCTCATCTG
13251 CAGGCCAAGG CCCCGAAAGC AACCGCCAAC TCTGTGTGGA GGGAGCTGGC
13301 CCTTGCATCC CAAGCCCGAC TGGCCGAGTG CCTCAGACGG AGCTCAGCAC
13351 CTGCACCCAC GGCCACTGCT GCTGGGAGTC AGACACAGAC ACCAGGATGG
13401 CCCTGTCCAA GTTCTGACAC CCACTTGCCA ACCCATTCCG GGAGCCTGTA
13451 GCCGTTCCCT GCTGGTTGAG AGTTGGGGGC TGGAAGGGGG GGGCCCTGC
13501 CTGGGGATCT CAAGGATGAG GCCCCAGCAT GGAGGATTGG GGGTAGAATT
13551 CCACCCTTGA ACCCCAGCAG ACAGTCCCTC CCCTGACTCC CACCTTGGTA
13601 GGGTGCTGCC TCAGGGAGCC ATAGAAGTCG GCTGTGTTTT GAGACGGCGA
13651 CAGAACCTGA CCCGTGGAGA CTGGGAGAGC CCAGCAGGCA CCTGTATTGC
13701 AGGGCTCCGA CTGCATGTGG CAGGGGCTCC TGCTGCGTCT GGGCCTGGAG
13751 GTCTCTCTCC CAGTGCTCTG TCCCAGTGT TCCTAGCAGA GGTATGCTTA
13801 CCAGCTGTCA GCACAGACCC TCCTGCTGCC TGGGTCCTGG CCCTCCTCCC
13851 CCATCTGCAC CCCCATCATA GGTAGAGACC CCACCCTCCC ATCGGTCCTA
13901 CATGGGGCTG TGCAGCTGGA GCCAAAAAGG CAAGGTAGAA AGAGGAGTGA
13951 TGGGGGAGGG GGATTGTTTC AGCTTCTCTG GTGCTGTGAT GCCCCAGGAG
```

FIGURE 3D

```
14001 AGTCCTAATC TAGGGAATGG GGTGGAGTAG GCAGATAATC CACCTCCCTA
14051 TCCCCCAGGC AAGGGCGGAG CATGTGTCTT GGGCCCACAC CTGCTTAGTT
14101 TATGAGGACC GGCTGCTTTC CAGTGGTAGC CCTTTTGCCA TGGAGGTCTG
14151 GGAGAGAGAG CAGAGGGCGG CAGGGCTAAG TTGGTGATCA TTGGGTTCTT
14201 CAGGACCTTC TATATCCCTC CTCGGTAACC CCCCAGCCCA ACCCCTTGGA
14251 ATCTTTCCTC CAGGCTTCCT GAGAGCCCTG GGGGTGGGAG GCTGTGGGAG
14301 GCTGTACATC TGAAATTCAC TTCAGTCCAA GTCATACCTA GGAAGCTGTC
14351 TGGGCAGCTG CTCGAGGGAG GCCCTGGCTC TGATCCCAGG CTGGATGGAG
14401 TGGCTGGAAG GAATGGTTCC AAACAACACC ACCGAGATCT CCCTCAGGCT
14451 GGCCAGGTTT TGCAGCTGGA ATTCTCCTCT TGGTCCCAGG GCGGGGCAGG
14501 GAATTCTAAG TGTCCACCCC AGGGAGGCAA GGGGCTGCTT TCCACTGTGG
14551 GTACCTGGTG ATCAGGGCAA GCTGTGGAGG GCCAGGGGTG GGGCTGAGAC
14601 TGGGCTGACA TCTAGAATCA CCTGCCACCT GGAGCCTCAG TAAAATGCCT
14651 GGGGTCCCTG CTGCCTCTCA ATCTCCAGAG CCATGTCCAT GGGGAGGTGG
14701 GCTCTGAAGG GCGAAGGTGG GAGAGCAGGG CCCCTGAGGC CTGGGTATCC
14751 AAGGAGGGGC ACGTGCACCT GATTCTCCTT GGGGCCCAGA GGAAGCTGAT
14801 GTCATGGCTG GACAAAGTCA CGGAGTAAAG CCAGCAAAGC CACCCTCTTC
14851 CTGTGTAGTC CTTACAGGCA TGACTGGAAA GTTGGGGGGC ATCTATGGTA
14901 GACATGGCAC AGCCATGAAG AGACCAGTGG GGTGGTGCAG GGTGGACTTG
14951 GGGACCCTAC CCCTGAAGAC TGAGGCCCTG CAGCTACCAG GTGGGCTAGA
15001 AGGTAACTGG AACAGGCCTG GGCACTTGTG CACCCATGTA GGAGCATGAG
15051 GGCCACACTC TTTTCACCTC AAAGCCCTTG AAGAGTGGGC AAAGACAGCA
15101 AGAGAGCTGC AGCCTGGGCC CGAGCTCAGA AACAGCTGTC GCCTCAGTCT
15151 GCGCACAGGC ATGCACCCCA GGGTAGTGCC TGCAGGGATG CATGTGTCCC
15201 CGTGGGGGTG CCTGTGCCAG GCAGGCCTCA GGTGCATGCC ATGCTCAGAA
15251 CCCTGCTGCC CTTTCTAGGC AGCCTCCTTG GGGCCCAAGC TCTGCTCCCT
15301 GGATCTGCCA CCTAGCAGAC GTGGGGAGCC TGACCCCATG CCTGTCATGG
15351 AACCCTCCTT GCCTGGTGTG TGTGCCTCCC CTCTTCACTG GGCACCTGGA
15401 TCCAGGCCCA CCTGTGTCCC TGACTCAGGG TGGTCCCAGG ACTGGCACCT
15451 ACTCTTTAGA GAGCCCAGC ATCTTTGATG TGGATTGGAG ACAATTGCCT
15501 GGTTCCCTGG GGCAGGTGAA GACTTGGTGC ACAAAGAAT GCCACAGTGG
15551 ATACGCCAGC AGGCCACATG GCTGGCCAAG CAATTATTAT TATGGATCCC
15601 TTGGGCTGTG GGCCTTCCCA TCCACCCCAC CACAACTGCC CAGGTAGCTG
15651 GAGCTGATCA TAAACAAGAA GGCTCTGGGC AGAGTCCATG GCACCAGCAC
15701 CAGCCAAGGC CCACTCCTGA AGACCCGAAG CCCAGCCCCT GGATGAAGGT
15751 CCTAAGGTCC TGAGGACTCC CCAGCCTGTG CAGGCCTGCA AACCCAGGCT
15801 GCCCACAACA GAAGGGGCTC TCGGCTTGTC TGGCCTCTCT GGCCTCCCAA
15851 GCAGGTGTGG GAGGGCGGGG CAAGTGTGGG CTGATCAGCT ACTCCATATG
15901 GCCAGGGTCC TGTGCTGGTG CCTGGCTGGG GGGCTGCATA GCCTGCACTG
15951 TCTCCTCCAG GCTGCCCCTG GGAATACCA CGTAGTGTGT GGAGTTCAGC
16001 CCTGGCAGCT CCCGCTGGTT CTCCTTGCTA TGCCGGATGC CATAGCCGAA
16051 ATACACTGCA AGTCCTAGAC AGGGCAGGAG GCAGGGCATG AGCCTGAGGT
16101 ACAGGTTCCA GCCCTTCCTG TCCTCTTTGC CCTCCTCCTG ACCCCGGTCC
16151 CAGCCTGGCC CCCACTCACC CATCAGCAGC CAGATGGAGA AGCGCACCCA
16201 GGTCAGATAG CTAAGTTTCA GCATGAGGCA GATGTTGAGG ACATGCTCA
16251 GGGCTGGAAT CAGGGGAACC ATGGGGATCT GAGGAGGCA AGGCAGGGCA
16301 GGGCTGGGCC GGGCTGCAGG AAAGATCTGC CAGCCCAGGG CTCACTTTCT
16351 CGGGAATCCA TAGAGCCTTT GTTCCTCACG GGAGATTGTG GAGACATGTG
16401 CTCACTCACC ATGCAGAAAG GGGTGCGGGA TGGGTGTGTG GTCCTCCCC
(SEQ ID NO: 3)
```

FEATURES:
Start: 2040
Exon: 2040-2095
Intron: 2096-2776
Exon: 2777-2927
Intron: 2928-4822
Exon: 4823-4894
Intron: 4895-9510
Exon: 9511-9586
Intron: 9587-9776
Exon: 9777-9870
Intron: 9871-9952
Exon: 9953-10033
Intron: 10034-10109
Exon: 10110-10251
Intron: 10252-10343
Exon: 10344-10453
Intron: 10454-12638
Exon: 12639-12732

FIGURE 3E

```
Intron:   12733-12844
Exon:     12845-12910
Intron:   12911-13085
Exon:     13086-13163
Intron:   13164-13253
Exon:     13254-13448
Stop:     13449
```

SNPs:

| DNA Position | Major | Minor | Domain | Protein Position | Major | Minor |
|---|---|---|---|---|---|---|
| 136 | C | T | Beyond ORF(5') | | | |
| 253 | T | C | Beyond ORF(5') | | | |
| 573 | C | T | Beyond ORF(5') | | | |
| 2000 | A | G | Beyond ORF(5') | | | |
| 2222 | G | C | Intron | | | |
| 2783 | G | T | Exon | 21 | A | A |
| 3199 | G | A | Intron | | | |
| 3307 | C | G | Intron | | | |
| 5012 | C | G | Intron | | | |
| 6169 | G | C | Intron | | | |
| 7647 | A | G | Intron | | | |
| 8638 | C | T | Intron | | | |
| 9409 | T | G | Intron | | | |
| 10504 | A | C | Intron | | | |
| 10971 | T | - | Intron | | | |
| 12609 | G | A | Intron | | | |
| 13367 | T | A | Exon | 378 | T | T |
| 14191 | T | C | Beyond ORF(3') | | | |
| 14227 | A | G | Beyond ORF(3') | | | |
| 15027 | T | C | Beyond ORF(3') | | | |
| 15441 | A | C | Beyond ORF(3') | | | |

Context:

| DNA Position | | |
|---|---|---|
| 136 | TCTCCAAGTCCATGGGTGCCTGGTAGGAGACAGGGGGATGAATGTGAACCCCTGCATGGC<br>TATAGCCACCTGCCTCCTCCCCTGCCCTGCATCACTACCTGGCCTATTTTTTGCCTCTAG<br>AAGCACTGCTTCCTA<br>[C,T]<br>GCTCCTTAGGACCACTGCCCGCATATGACAGATAAGAACATCGAGGCTAAGGCAACGCAA<br>ATCTTTTCCTTAAAGTCATACAGCTGTCAAAAGAAAGCTGGACAACCTGGGCAACATAGC<br>GAGATAAAAAATTATTTAAATTAGCCAGATGTGGTAGCCCCCTGTAGTCTCAGCGACTCA<br>GGAGGCTGAGGCAGGAGGCTCACCAGAGTGCAGAGTTCAAGGATGCAGTGAGCTATGATC<br>CTGCCACTGCACTGAAAGCTGGGTGACAGAGCAAGACCCTGGCTCTAATAAATGAATACA | (SEQ ID NO:5) |
| 253 | TCTCCAAGTCCATGGGTGCCTGGTAGGAGACAGGGGGATGAATGTGAACCCCTGCATGGC<br>TATAGCCACCTGCCTCCTCCCCTGCCCTGCATCACTACCTGGCCTATTTTTTGCCTCTAG<br>AAGCACTGCTTCCTATGCTCCTTAGGACCACTGCCCGCATATGACAGATAAGAACATCGA<br>GGCTAAGGCAACGCAAATCTTTTCCTTAAAGTCATACAGCTGTCAAAAGAAAGCTGGACA<br>ACCTGGGCAACA<br>[T,C]<br>AGCGAGATAAAAAATTATTTAAATTAGCCAGATGTGGTAGCCCCCTGTAGTCTCAGCGAC<br>TCAGGAGGCTGAGGCAGGAGGCTCACCAGAGTGCAGAGTTCAAGGATGCAGTGAGCTATG<br>ATCCTGCCACTGCACTGAAAGCTGGGTGACAGAGCAAGACCCTGGCTCTAATAAATGAAT<br>ACATAAAGTCTCACAGCTAGTGGTAGCTAATCCTGCCAGAGTCAGGCCTCTACCTGTCTG<br>ATGACAAATGGCACACTATGTCTTTTAACCTGATTGCAGACCACAAATGTTTTGTGAATA | (SEQ ID NO:6) |
| 573 | TAAATTAGCCAGATGTGGTAGCCCCCTGTAGTCTCAGCGACTCAGGAGGCTGAGGCAGGA<br>GGCTCACCAGAGTGCAGAGTTCAAGGATGCAGTGAGCTATGATCCTGCCACTGCACTGAA<br>AGCTGGGTGACAGAGCAAGACCCTGGCTCTAATAAATGAATACATAAAGTCTCACAGCTA<br>GTGGTAGCTAATCCTGCCAGAGTCAGGCCTCTACCTGTCTGATGACAAATGGCACACTAT<br>GTCTTTTAACCTGATTGCAGACCACAAATGTTTTGTGAATATTTTCCCCAGGGAAAAAAC<br>[C,T] | |

FIGURE 3F

```
       GGAAGTAGTTCTAAATTCTATACATCCATTATATTAGTTTTACCTGTGGATTGGGAAAAC
       CCAGCTCTGATTGCATTTCAGGGCGGGACAGCCTTTGGTGCACTGTCTGGCGGGATTTTC
       CATTTTAACCTCCTTCTAGAAGCGCCTTCTCATGGTAAAGTTCCTGATGCCGCCAGGAGC
       GCCGAGGAGAGGGCAGGGGGCTGGAGACGCCCCGCAGAGGGCTACGTGCCCTGCTGGACA
       GAGGTCTCCTGCCTCCTCGGCGGCGCCAGCCCACCTCCCACAACCCCTGCGGGAGAAGCC       (SEQ ID NO:7)

2000   CTCCTCTCACAGCACTGATAACAGCTGTCCGTCTCCACCCTCCCACCACCTCCACTCCCA
       CCCCAGGAAGTGAGGCCAGAGGGCAGGGACAGAGCTGCTGCTGTTCTCTGTGTGCCAGGG
       CCCAGCAAAGGGAATGTAGGGAGGGTGGGAGGTGCAGGGCAGCTGGGATTAGGGGTTGAG
       GGCTGGGTGTTGGAGGCTGGATCTGGATCCTGCTTTAGTGGAAGTGTCCCTTTAACAGCA
       ACTGGCCTGGCTCGGGCCCTGCTTTGCCTCCTGTTCAGCTGCGGCTGCAGCTGCC
       [A,G]
       TGCTGACTCATGTGCCCGCAGCTAGCAGGAGCTGGCAGCATGGGCTCCCAGGGGCTACG
       ACAGGCTGGGGGCTTCTGGATTATAAGACGGAGAAGTATGTGATGACCAGGAACTGGCGG
       GTGGGCGCCCTGCAGAGGCTGCTGCAGTTTGGGATCGTGGTCTATGTGGTAGGGTAAGAG
       AGAAGAGCTTTTGGCCAGGCTGGAGGGGCAAGGGAAGAGGTGGGGGGTGGGGCTTGGTCC
       TGCTGGGTTGAAGTTGAGGGTTGGGCTGTTTAGGGGCTGGAGTGGAAGGGGGCAGATTGG       (SEQ ID NO:8)

2222   AGTGTCCCTTTAACAGCAACTGGCCTGGCCTGGCTCGGGCCCTGCTTTGCCTCCTGTTCA
       GCTGCGGCTGCAGCTGCCATGCTGACTCATGTGCCCGCAGCTAGCAGGAGCTGGCAGCAT
       GGGCTCCCCAGGGGCTACGACAGGCTGGGGGCTTCTGGATTATAAGACGGAGAAGTATGT
       GATGACCAGGAACTGGCGGGTGGGCGCCCTGCAGAGGCTGCTGCAGTTTGGGATCGTGGT
       CTATGTGGTAGGGTAAGAGAGAAGAGCTTTTGGCCAGGCTGGAGGGGCAAGGGAAGAGGT
       [G,C]
       GGGGGTGGGGCTTGGTCCTGCTGGGTTGAAGTTGAGGGTTGGGCTGTTTAGGGGCTGGAG
       TGGAAGGGGGCAGATTGGGACGGGGTTGGGGAGAGCTAGGCGATACAAGACAGGAGAGCA
       AGAACAAGCTGTGTGTTTGTCCTGTGTGTCCACTTGCCTCCTTCCCAGGCCCCCACCCAG
       GCCCCACCCAGGGGGCACATGACATAGTCCTTAACATCTGTGAGAGCTGGAGCACTAGGC
       CCCCAGAGAGACCACCAGCTGTATCTCGGGTCAGGAGAGTCTGTAAGGGGGAAGCTGGAT       (SEQ ID NO:9)

2783   GTATCTCGGGTCAGGAGAGTCTGTAAGGGGGAAGCTGGATCTAGTCAGGCTGGGGGTGGG
       TGCTGGCTAGTGAAGGTGATTGTCTGAGGGCATTGGCTCTCTGATGCATGGCTGGAGCTT
       CTGTCTCATTCAGGGGGTCTGGAGTGGGAAGTGGGGCCAGAGAGGAGGTGGGGCCTTCGA
       TGTTGGGCCGGGAGCCTGTAGGGTGTGGGGGGAGAACTGAGCATGTAGGGCTCAGCTCCG
       CCCCTGTCACTACACGCTGGGGACACACCACACTGCCCGACTTCTCCTCCCCAGGTGGGC
       [G,T]
       CTCCTCGCCAAAAAAGGCTACCAGGAGCGGGACCTGGAACCCCAGTTTTCCATCATCACC
       AAACTCAAAGGGGTTTCCGTCACTCAGATCAAGGAGCTTGGAAACCGGCTGTGGGATGTG
       GCCGACTTCGTGAAGCCACCTCAGGTGGGGGCCCTGATGTTGCTGACGGGGGCGCAAGTC
       CTTTCCCCACTGACAGCCTGAACACCCGCCATGCAGCCAGTGTGTGCGAGAGAGAAGCAT
       GTGATGCCAGAGACGGCTGCGGGTTCTCAGGAAGGGCTTCACAGAGGAGTGGCACCTGGA       (SEQ ID NO:10)

3199   ATGTGGCCGACTTCGTGAAGCCACCTCAGGTGGGGGCCCTGATGTTGCTGACGGGGGCGC
       AAGTCCTTTCCCCACTGACAGCCTGAACACCCGCCATGCAGCCAGTGTGTGCGAGAGAGA
       AGCATGTGATGCCAGAGACGGCTGCGGGTTCTCAGGAAGGGCTTCACAGAGGAGTGGCAC
       CTGGACAGGACTTTCAGGGATGTGTAGGAGGTTTTGGGGTGGAAAAAGGGGCCACTCAAG
       AAGCCAGGCCAGGGTTGGACGTGCTGGCTCACGCCTGTAATCCCAGCACTTTGGGAGGCC
       [G,A]
       AGGCAGGTGGATCACGAGATTGAGAGTATCCTGGCTAACACGGTGAAACCCCATCTCTAT
       TAAAAATACAAAAAATTAGCCGGGCATGGTGGTGGGCGCCTGTAGTCCCAGCTACTCGGG
       AGGCTGGGGCAGGAGAATGGCATGAACCCGGGAGGTGGAGCTTGCAGTGAGCCGAGATTG
       CACCACTGCACTCCAGCCTGGGTGGCAAAGCGAGACTCTGTCTCAAAAAAAAAAAAAAAA
       AGCCAGGCCAGAGAAACTGCATTTCCAAAGACTGCCAACAGAAAAGAAGGGAGTGTCCAG       (SEQ ID NO:11)

3307   GTGCGAGAGAGAAGCATGTGATGCCAGAGACGGCTGCGGGTTCTCAGGAAGGGCTTCACA
       GAGGAGTGGCACCTGGACAGGACTTTCAGGGATGTGTAGGAGGTTTTGGGGTGGAAAAAG
       GGGCCACTCAAGAAGCCAGGCCAGGGTTGGACGTGCTGGCTCACGCCTGTAATCCCAGCA
       CTTTGGGAGGCCGAGGCAGGTGGATCACGAGATTGAGAGTATCCTGGCTAACACGGTGAA
       ACCCCATCTCTATTAAAAATACAAAAAATTAGCCGGGCATGGTGGTGGGCGCCTGTAGTC
       [C,G]
       CAGCTACTCGGGAGGCTGGGGCAGGAGAATGGCATGAACCCGGGAGGTGGAGCTTGCAGT
       GAGCCGAGATTGCACCACTGCACTCCAGCCTGGGTGGCAAAGCGAGACTCTGTCTCAAAA
       AAAAAAAAAAAAGCCAGGCCAGAGAAACTGCATTTCCAAAGACTGCCAACAGAAAAGAA
       GGGAGTGTCCAGGACTAATGGCTTGAGCTTGAGAGTGGTGTGAGGTGCTGGGGCATGGAA
       CTTCCCTGTAGCCCTGCTCCCTGACCTGGGGCACTACGGTCAGGTGCTGCTCCTCCCCTC       (SEQ ID NO:12)

5012   TTAATGACTTGATGGGGCCAACATCCCTTCCCTCATAAACCAGGCTGCCGGCTTCCGGCC
       TTTCCAGTCAACACGAGCCCAGCCAGGCCAACCTTGAGACTTGCCTCCTAGGGAGAGAAC
       GTGTTCTTCTTGGTGACCAACTTCCTTGTGACGCCAGCCCAAGTTCAGGGCAGATGCCCA
       GAGGTGAGTTTACCCAGGATCCTCCCAGCGGGTCCCTTGTTCCTCCATCAGCCCCAGGTG
```

FIGURE 3G

```
        GCCACCCGTGTTTCCCTTTCCCCTTCCCAGGTGGCTGAAGGCTCAGCCTGTGCTCGGTGT
        [C,G]
        CCCCAGGCACTGGGCTACATCTTTTCCTGAATCATTATGTTCAGTCTTCACATATCCCCT
        GCCTGGTAGGAAGTCCTGTGATCCCCATTTCAGAGGAGAAGACTGAGGCTCAGTGAGGTT
        GAGTCACTTTCTTAAGGCCTCCAGGCCTGTGGGTGACAGGACCCCGAGCTCTGGGCAGCA
        GCAGTTCCCATGAGGTGTCCAGGCCCTCCCATCCTGGTCCTGCCTCTGGGTACTCTCCAG
        GTTGGTAGTGTGACACCCAGAGCTGCGCACATGCTCAGGGAGGTTCTAATAGCAAGAGCC      (SEQ ID NO:13)

6169    CTTGCCTGGGGATGTCCCTGGGATCCTGCATCTGTCACAGAGCATGCTCATTCTCTCCAG
        CTGTGAATTTTGTTTGAACTATTGGGACTCAGGACATAGTCCTGAAAGTTTACCTCCACA
        GTGACATCTTTAGGCAAGTCCAACATTTACGTGCCTCCTGGGCTGGAGGGTCGTTGTGCA
        GACAGCTGTCCCCTGAGCCCTGGTGGCTGGTCCTAGCACAGTTGCTGGAGACATCCCATG
        TCCGTAGTTGGAAATATGCACAAAGGATTGCTTACTCTTTTTGTTTGTTTGTTTTTTTGA
        [G,C]
        ATGGAGTCTTGCTCTTGTCCCCAAGGCTGGAGTTCAATGGCACGATCTCGGCTCACTGCA
        ACCTCCGCCTCCTGGGTTCAAGCAGTTCTCCTGCTCACCCCCTGAGTAGCTGGGATTACA
        GGTGCCCGCCACTGTGCCCAGCTAATTTTTGTATTTTAAGTAGAGACGGGGTTTCACCAT
        GTTGGCCAGGCTGGTCTCGAACTCCTGGCCTCAGGTGACCCACCAGCCTCGGCCTCTCAA
        AGTGCTGGGATTACAGGCGTGAGCCTGCCGAGAGCTTGGTCGGGGAGACCTGAACCCAGC     (SEQ ID NO:14)

7647    AGGTGGCAGGTCCGATGATGGGACAGAGGCTGTAGGTGGGGGACCTAGGGCTGCACTTGA
        GCAGAATCTTTTTTTTTTTTTTCTTTTTTTTTTTTTGAGACAGAGTCTCGCTCTGTCAC
        CCAGGCTGGAGTGCAGTGGCGTGATCTCGGCTCACTGCACACCTCCACCTCCTTGGTTCA
        AGCGATTCTCCTGCCTCAGCCTCCCAAGTAGGTGGGACTACAGGCACACACCACCACACT
        CGGCTAATTTTTGTATTTTTAATAGAGACAGGGTTTTGCTGTGTCGGCCAGGCTGGTCTC
        [A,G]
        AACTCCTGACCTCAGGTAATCCGCCCACCTTGGCTTCTCAAAGTGTTGGGATTACAGGTG
        TGCCAGGCCAAGCAGAATCTTAAAAAAAGGTGGGGAGAAGCTGGTGAGCAGGTGGATTTG
        GTTGAAGCAGGATGTCGACACAGAGGGGGCTTGGTGGGTAAAGGCCCTGAGCTGTGTGAG
        GTGAGGTGCCTTTAGGGCTACCTGCCACTGGGTGGAGCTGAAGTGAAGATTTGGACTGGG
        GTGGGAAGAAGGTAGTTCAGGATTTCAGGGGCCCCTGTAAGCCCCACTAAGGAGCTAAAC     (SEQ ID NO:15)

8638    ACAAAGAAGCAGAGCATGTGGCTCTGCTCCGACCTCCACCCAATCACGACGGCCCTGTCT
        TTCAGAAAGTCCCACCGCCTCATTCTGGCTTCTCAGAGGCCCTCAGCCTTCCTTGCGCCC
        CTGGTGCTGGTGTTCTTCCTGCTGCCCCTGAGCTGAGTGCCCTGGGCAGCAGTGTCCATC
        CTCAGTTGGGGCAGGACCATGCCTGGGAGAGTGCCCGATGCTCAAGGGTGCCTTCGTCTC
        TGGGGTCTGGGACCCCAGAAAGCTCACCTGTCCTCCCCTTCTGCCAGAGCCCCATAGTCC
        [C,T]
        ATGCCTCTGTGCAGGCATTAATGTCCCCAGGTTACAGAAGAGCGAGCAGGAAGGAGTAGC
        CTGTGGTCCCTCAGCAAGGGTGTGGGGTCCTGCTTCAATACCCAAGCCCCTGACTCTAGG
        GCCCTGATCTTTGTCAGCTATGTCCCCATGCCGGGCATCAAAAACTCACCCTCCCAAGGT
        ATCTTCACCTTCCCTGATCTGTCATCCAAATTGACCAGAGGAGCTAGACCTGGAAGAAT
        CACTTCCGCATCCACCAGGGACAGAACTGTCAGGAGGGAAGGGGCAGGGTGCGTTGTCTC     (SEQ ID NO:16)

9409    TGAGGTGAGAGGATTGCTTAAGCCCGGGAGGGCGAGGCTGTAGTGAGCCATGATCATACC
        ACTGCACTAGAGCCTGGACAACAGAGTGAGACCGAATCACTAAAAATAAATTTTTTGAAA
        AAGGAGGAAAGGGGTCTCCCTTTGTCTTTGAAATACAGTACTGTACCTTCATCTGGCCAG
        GGCATTGCTCCGCTCCCTCCTCTGACCACCTCCTTTTATTTGCACCCTCCAGCTTTCCTG
        TGTGGCCCCACACTCAGGGTACTCTGGCGGCGGGGTGGTGAGGTTGTTTAAGGTGGGAAG
        [T,G]
        GGGCCTGTCCTTCCCACCTTGAACCTCCCTGCCTTTGAGACTGGGCTGTGGAGGGGAGAC
        ATCCCCTGTGCCATTGGTGACTGCTCTCTCTCCCACCTCAGCACCCGTCCGTCCCACTGG
        CTAACTGCTGGGTCGACGAGGACTGCCCCGAAGGGGAGGGAGGCACACACAGCCACGGTA
        ACTGTGGGCTCTGTCTTCCAGTGCCCCTAGCAGGGTGGGGGCCGGGCTGGGATCCTGGGT
        GGCTCCTGAGTGCAGGCCCTGCTCGCCTCTGTCCCTGCATCTCTCTTTCTGCCAACAACC      (SEQ ID NO:17)

10504   GACCTCGTGGCCAAGGCTGGAGGGACCTTCGAGGACCTGGCGTTGCTGGTGGGTCCCAAG
        TTGGGGGCAGGGTTCCTAGAGGGCTCTGGGAGAGGGTCCCGGGCCCACCCACCGGTGGAA
        AAGCTATGTGCTATGTGCAGGGTGGCTCTGTAGGCATCAGAGTTCACTGGGATTGTGACC
        TGGACACCGGGGACTCTGGCTGCTGGCCTCACTACTCCTTCCAGCTGCAGGAGAAGAGCT
        ACAACTTCAGGTGAGGCCCCACTGCTCCCAGTGCCCAGCTGCTGGGCCCATCGCCCTCTC
        [A,C]
        CTGTGGCGGCCAGGACAGACCACACCCAGGCCCAGGCCTCTAGATATTCCACTACGTGTG
        CAAGGGGGTCCCAGGAGCAGGAGAGAGCTGTTCTCAACCCCACATCCTCCAGCACAGGCT
        CCGTCCTGCTGCCCCAAGTCCTGAGCCCTCCACCCCATCTGTCCCAGGCCCCTGCCCAGC
        TCAGGCTCCTCACTGCCAGCCCTTCCTCCACCCCACCTCGCTTCTAGTATCTCCCCTCCA
        CAGCAATGGGGTGTTTCATTTTTACTTTCCCCTTCTCCCCTTCAGCTTTGTTTTTTTTTT     (SEQ ID NO:18)

10971   GGCCCCTGCCCAGCTCAGGCTCCTCACTGCCAGCCCTTCCTCCACCCCACCTCGCTTCTA
        GTATCTCCCCTCCACAGCAATGGGGTGTTTCATTTTTACTTTCCCCTTCTCCCCTTCAGC
```

FIGURE 3H

```
         TTTGTTTTTTTTTTTTAAGACAGAATCTCATTCTGTCACCCAGGCTGGAGTGCAGTGGC
         CCGACCTCGGCTCACTGTAACCTCTGCTTCCTGGGTTCAACCGATTCTCCTTCCTCAGCC
         TCCTGAGTAGCTGGAATTACAGGTGCTCGCCACTACTCCCAGCTAATTTTTATATTTTGG
         [T,-]
         AGATAGAGATGGGTTTTCACAATGTTGGCCAGGCTGGTCTCAAACCCCTGACCTCAGGTG
         ATCCACCCACCTCAGCCTCCCGAAGGGCTAGGATTACAGACGTAAACCACCATGTCTGGC
         CTCCCTTCCGCTTTTACCTAAACTTTTTTTTTTTTTGAGATGGAGTCTCACTCTGTCG
         CCCAGGCTGGAGTACAGTGGCGGGATCTCAGCTCACTGCAAGTTCCGCTTCCCGTGTTCA
         CGCCATTCTCCTGCCTCAGCCTCCCAAGTAGCTGGGACTACGGGTGCACGCCTCCACGCC       (SEQ ID NO:19)

12609    CCAGGAAGTCTACCCCAGTTCCCAGGGAAGAGTGAGTTCCCATCTCTGGAATCCCTCAGC
         CCTGAGCCTGCCCCTTCACATCCCCCGCTGCTGGGTCTGTTTAGGGACTCCTCTGTCCCC
         CGTCCTCTCAGCAGGCAGGGAACTTCTGAGGGACAGGTCTTCGTTTGCTTTTTCTGTTTT
         CTCACCAATTACATAGGGCTGAGACCCAGGACTCAGGCTTGGGCTGGGGGTTTATAGAGT
         CAATTGACAAGTTGGACAGAGGTCTGGCAGGGCCAGCCCCACCTGGGGGTGGGCAAAGCA
         [G,A]
         GTCACCAGAGCCTTCTTTCCTGCCCACAGGACAGCCACTCACTGGTGGGAGCAACCGGGT
         GTGGAGGCCCGCACCCTGCTCAAGCTCTATGGAATCCGCTTCGACATCCTCGTCACCGGG
         CAGGTAGGCACAGGTAGGGGTCAGGCCGGGGATGGGATGGGGCAGGCAGACAGGGCTGGA
         GGAGGCATGAGGCTGACAGTCGTGGGCTGAGAGGTTCAGCTCAGATCTCTCTCAGGCAGG
         GAAGTTCGGGCTCATCCCCACGGCCGTCACACTGGGCACCGGGGCAGCTTGGCTGGGCGT       (SEQ ID NO:20)

13367    TTGGCCCTGCCTCTCCCAGGTCACCTTTTTCTGTGACCTGCTACTGCTGTATGTGGATAG
         AGAAGCCCATTTCTACTGGAGGACAAAGTATGAGGAGGTGAGCTGAGGTCGCTCTGCTTG
         GACCCTGGGTTCTGCCACACTTAGGAAGATGTTGGCTGGATCCCTGACCTGCTGTCCTCA
         TCTGCAGGCCAAGGCCCCGAAAGCAACCGCCAACTCTGTGTGGAGGGAGCTGGCCCTTGC
         ATCCCAAGCCCGACTGGCCGAGTGCCTCAGACGGAGCTCAGCACCTGCACCCACGGCCAC
         [T,A]
         GCTGCTGGGAGTCAGACACAGACACCAGGATGGCCCTGTCCAAGTTCTGACACCCACTTG
         CCAACCCATTCCGGGAGCCTGTAGCCGTTCCCTGCTGGTTGAGAGTTGGGGGCTGGGAAG
         GGCGGGGCCCTGCCTGGGGATCTCAAGGATGAGGCCCCAGCATGGAGGATTGGGGGTAGA
         ATTCCACCCTTGAACCCCAGCAGACAGTCCCTCCCCTGACTCCCACCTTGGTAGGGTGCT
         GCCTCAGGGAGCCATAGAAGTCGGCTGTGTTTTGAGACGGCGACAGAACCTGACCCGTGG       (SEQ ID NO:21)

14191    ATCGGTCCTACATGGGGCTGTGCAGCTGGAGCCAAAAAGGCAAGGTAGAAAGAGGAGTGA
         TGGGGGAGGGGGATTGTTTCAGCTTCTCTGGTGCTGTGATGCCCCAGGAGAGTCCTAATC
         TAGGGAATGGGGTGGAGTAGGCAGATAATCCACCTCCCTATCCCCCAGGCAAGGGCGGAG
         CATGTGTCTTGGGCCCACACCTGCTTAGTTTATGAGGACCGGCTGCTTTCCAGTGGTAGC
         CCTTTTGCCATGGAGGTCTGGGAGAGAGAGCAGAGGGCGGCAGGGCTAAGTTGGTGATCA
         [T,C]
         TGGGTTCTTCAGGACCTTCTATATCCCTCCTCGGTAACCCCCCAGCCCAACCCCTTGGAA
         TCTTTCCTCCAGGCTTCCTGAGAGCCCTGGGGGTGGGAGGCTGTGGGAGGCTGTACATCT
         GAAATTCACTTCAGTCCAAGTCATACCTAGGAAGCTGTCTGGGCAGCTGCTCGAGGGAGG
         CCCTGGCTCTGATCCCAGGCTGGATGGAGTGGCTGGAAGGAATGGTTCCAAACAACACCA
         CCGAGATCTCCCTCAGGCTGGCCAGGTTTTGCAGCTGGAATTCTCCTCTTGGTCCCAGGG       (SEQ ID NO:22)

14227    AAGGCAAGGTAGAAAGAGGAGTGATGGGGGAGGGGGATTGTTTCAGCTTCTCTGGTGCTG
         TGATGCCCCAGGAGAGTCCTAATCTAGGGAATGGGGTGGAGTAGGCAGATAATCCACCTC
         CCTATCCCCCAGGCAAGGGCGGAGCATGTGTCTTGGGCCCACACCTGCTTAGTTTATGAG
         GACCGGCTGCTTTCCAGTGGTAGCCCCTTTTGCCATGGAGGTCTGGGAGAGAGAGCAGAGG
         GCGGCAGGGCTAAGTTGGTGATCATTGGGTTCTTCAGGACCTTCTATATCCCTCCTCGGT
         [A,G]
         ACCCCCCAGCCCAACCCCTTGGAATCTTTCCTCCAGGCTTCCTGAGAGCCCTGGGGGTGG
         GAGGCTGTGGGAGGCTGTACATCTGAAATTCACTTCAGTCCAAGTCATACCTAGGAAGCT
         GTCTGGGCAGCTGCTCGAGGGAGGCCCTGGCTCTGATCCCAGGCTGGATGGAGTGGCTGG
         AAGGAATGGTTCCAAACAACACCACCGAGATCTCCCTCAGGCTGGCCAGGTTTTGCAGCT
         GGAATTCTCCTCTTGGTCCCAGGGCGGGCAGGGAATTCTAAGTGTCCACCCCAGGGAGG       (SEQ ID NO:23)

15027    AGGGCCCCTGAGGCCTGGGTATCCAAGGAGGGGCACGTGCACCTGATTCTCCTTGGGGCC
         CAGAGGAAGCTGATGTCATGGCTGGACAAAGTCACGGAGTAAAGCCAGCAAAGCCACCCT
         CTTCCTGTGTAGTCCTTACAGGCATGACTGGAAAGTTGGGGGGCATCTATGGTAGACATG
         GCACAGCCATGAAGAGACCAGTGGGGTGGTGCAGGGTGGACTTGGGGACCCTACCCCTGA
         AGACTGAGGCCCTGCAGCTACCAGGTGGGCTAGAAGGTAACTGGAACAGGCCTGGGCACT
         [T,C]
         GTGCACCCATGTAGGAGCATGAGGGCCACACTCTTTTCACCTCAAAGCCCTTGAAGAGTG
         GGCAAAGACAGCAAGAGAGCTGCAGCCTGGGCCCGAGCTCAGAAACAGCTGTCGCCTCAG
         TCTGCGCACAGGCATGCACCCCAGGGTAGTGCCTGCAGGGATGCATGTGTCCCCGTGGGG
         GTGCCTGTGCCAGGCAGGCCTCAGGTGCATGCCATGCTCAGAACCCTGCTGCCCTTTCTA
         GGCAGCCTCCTTGGGGCCCAAGCTCTGCTCCCTGGATCTGCACCCTAGCAGACGTGGGGA       (SEQ ID NO:24)
```

FIGURE 3I

15441    GCCTCAGTCTGCGCACAGGCATGCACCCCAGGGTAGTGCCTGCAGGGATGCATGTGTCCC
         CGTGGGGGTGCCTGTGCCAGGCAGGCCTCAGGTGCATGCCATGCTCAGAACCCTGCTGCC
         CTTTCTAGGCAGCCTCCTTGGGGCCCAAGCTCTGCTCCCTGGATCTGCCACCTAGCAGAC
         GTGGGGAGCCTGACCCCATGCCTGTCATGGAACCCTCCTTGCCTGGTGTGTGTGGCTCCC
         CTCTTCACTGGGCACCTGGATCCAGGCCCACCTGTGTCCCTGACTCAGGGTGGTCCCAGG
         [A,C]
         CTGGCACCTACTCTTTAGAGAGCCCCAGCATCTTTGATGTGGATTGGAGACAATTGCCTG
         GTTCCCTGGGGCAGGTGAAGACTTGGTGCCACAAAGAATGCCACAGTGGATACGCCAGCA
         GGCCACATGGCTGGCCAAGCAATTATTATTATGGATCCCTTGGGCTGTGGGCCTTCCCAT
         CCACCCCACCACAACTGCCCAGGTAGCTGGAGCTGATCATAAACAAGAAGGCTCTGGGCA
         GAGTCCATGGCACCAGCACCAGCCAAGGCCCACTCCTGAAGACCCGAAGCCCAGCCCCTG    (SEQ ID NO:25)

Chromsome map:
Chromosome No: 22

FIGURE 3J

ISOLATED HUMAN G-PROTEIN COUPLED RECEPTORS, NUCLEIC ACID MOLECULES ENCODING HUMAN GPCR PROTEINS, AND USES THEREOF

FIELD OF THE INVENTION

The present invention is in the field of G-Protein coupled receptors (GPCRs) that are related to the P2X-like purinergic receptor subfamily, recombinant DNA molecules, and protein production. The present invention specifically provides novel GPCR peptides and proteins and nucleic acid molecules encoding such peptide and protein molecules, all of which are useful in the development of human therapeutics and diagnostic compositions and methods.

BACKGROUND OF THE INVENTION

G-Protein Coupled Receptors

G-protein coupled receptors (GPCRs) constitute a major class of proteins responsible for transducing a signal within a cell. GPCRs have three structural domains: an amino terminal extracellular domain, a transmembrane domain containing seven transmembrane segments, three extracellular loops, and three intracellular loops, and a carboxy terminal intracellular domain. Upon binding of a ligand to an extracellular portion of a GPCR, a signal is transduced within the cell that results in a change in a biological or physiological property of the cell. GPCRs, along with G-proteins and effectors (intracellular enzymes and channels modulated by G-proteins), are the components of a modular signaling system that connects the state of intracellular second messengers to extracellular inputs.

GPCR genes and gene-products are potential causative agents of disease (Spiegel et al., *J. Clin. Invest.* 92:1119–1125 (1993); McKusick et al., *J. Med. Genet.* 30:1–26 (1993)). Specific defects in the rhodopsin gene and the V2 vasopressin receptor gene have been shown to cause various forms of retinitis pigmentosum (Nathans et al., *Annu. Rev. Genet.* 26:403–424(1992)), and nephrogenic diabetes insipidus (Holtzman et al., *Hum. Mol. Genet.* 2:1201–1204 (1993)). These receptors are of critical importance to both the central nervous system and peripheral physiological processes. Evolutionary analyses suggest that the ancestor of these proteins originally developed in concert with complex body plans and nervous systems.

The GPCR protein superfamily can be divided into five families: Family I, receptors typified by rhodopsin and the β2-purinergic receptor and currently represented by over 200 unique members (Dohlman et al., *Annu. Rev. Biochem.* 60:653–688 (1991)); Family II, the parathyroid hormone/calcitonin/secretin receptor family (Juppner et al., *Science* 254:1024–1026 (1991); Lin et al., *Science* 254:1022–1024 (1991)); Family III, the metabotropic glutamate receptor family (Nakanishi, *Science* 258 597:603 (1992)); Family IV, the cAMP receptor family, important in the chemotaxis and development of *D. discoideum* (Klein et al., *Science* 241: 1467–1472 (1988)); and Family V, the fungal mating pheromone receptors such as STE2 (Kujan, *Annu. Rev. Biochem.* 61:1097–1129 (1992)).

There are also a small number of other proteins that present seven putative hydrophobic segments and appear to be unrelated to GPCRs; they have not been shown to couple to G-proteins. *Drosophila* expresses a photoreceptor-specific protein, bride of sevenless (boss), a seven-transmembrane-segment protein that has been extensively studied and does not show evidence of being a GPCR (Hart et al., *Proc. Natl. Acad. Sci. USA* 90:5047–5051 (1993)). The gene frizzled (fz) in *Drosophila* is also thought to be a protein with seven transmembrane segments. Like boss, fz has not been shown to couple to G-proteins (Vinson et al., *Nature* 338:263–264 (1989)).

G proteins represent a family of heterotrimeric proteins composed of α, β and γ subunits, that bind guanine nucleotides. These proteins are usually linked to cell surface receptors, e.g., receptors containing seven transmembrane segments. Following ligand binding to the GPCR, a conformational change is transmitted to the G protein, which causes the α-subunit to exchange a bound GDP molecule for a GTP molecule and to dissociate from the βγ-subunits. The GTP-bound form of the α-subunit typically functions as an effector-modulating moiety, leading to the production of second messengers, such as cAMP (e.g., by activation of adenyl cyclase), diacylglycerol or inositol phosphates. Greater than 20 different types of α-subunits are known in humans. These subunits associate with a smaller pool of β and γ subunits. Examples of mammalian G proteins include Gi, Go, Gq, Gs and Gt. G proteins are described extensively in Lodish et al., *Molecular Cell Biology*, (Scientific American Books Inc., New York, N.Y., 1995), the contents of which are incorporated herein by reference. GPCRs, G proteins and G protein-linked effector and second messenger systems have been reviewed in *The G-Protein Linked Receptor Fact Book*, Watson et al., eds., Academic Press (1994).

Aminergic GPCRs

One family of the GPCRS, Family II, contains receptors for acetylcholine, catecholamine, and indoleamine ligands (hereafter referred to as biogenic amines). The biogenic amine receptors (aminergic GPCRs) represent a large group of GPCRs that share a common evolutionary ancestor and which are present in both vertebrate (deuterostome), and invertebrate (protostome) lineages. This family of GPCRs includes, but is not limited to the 5-HT-like, the dopamine-like, the acetylcholine-like, the adrenaline-like and the melatonin-like GPCRs.

Dopamine Receptors

The understanding of the dopaminergic system relevance in brain function and disease developed several decades ago from three diverse observations following drug treatments. These were the observations that dopamine replacement therapy improved Parkinson's disease symptoms, depletion of dopamine and other catecholamines by reserpine caused depression and antipsychotic drugs blocked dopamine receptors. The finding that the dopamine receptor binding affinities of typical antipsychotic drugs correlate with their clinical potency led to the dopamine overactivity hypothesis of schizophrenia (Snyder, S. H., *Am J Psychiatry* 133, 197–202 (1976); Seeman, P. and Lee, T., *Science* 188, 1217–9 (1975)). Today, dopamine receptors are crucial targets in the pharmacological therapy of schizophrenia, Parkinson's disease, Tourette's syndrome, tardive dyskinesia and Huntington's disease. The dopaminergic system includes the nigrostriatal, mesocorticolimbic and tuberoinfindibular pathways. The nigrostriatal pathway is part of the striatal motor system and its degeneration leads to Parkinson's disease; the mesocorticolimbic pathway plays a key role in reinforcement and in emotional expression and is the desired site of action of antipsychotic drugs; the tuberoinfundibular pathways regulates prolactin secretion from the pituitary.

Dopamine receptors are members of the G protein coupled receptor superfamily, a large group proteins that share a seven helical membrane-spanning structure and transduce signals through coupling to heterotrimeric guanine nucleotide-binding regulatory proteins (G proteins). Dopamine receptors are classified into subfamilies: D1-like (D1 and D5) and D2-like (D2, D3 and D4) based on their different ligand binding profiles, signal transduction properties, sequence homologies and genomic organizations (Civelli, O., Bunzow, J. R. and Grandy, D. K., *Annu Rev Pharmacol Toxicol* 33, 281–307 (1993)). The D1-like receptors, D1 and D5, stimulate cAMP synthesis through coupling with Gs-like proteins and their genes do not contain introns within their protein coding regions. On the other hand, the D2-like receptors, D2, D3 and D4, inhibit cAMP synthesis through their interaction with Gi-like proteins and share a similar genomic organization which includes introns within their protein coding regions.

Serotonin Receptors

Serotonin (5-Hydroxytryptamine; 5-HT) was first isolated from blood serum, where it was shown to promote vasoconstriction (Rapport, M. M., Green, A. A. and Page, I. H., *J Biol Chem* 176,1243–1251 (1948). Interest on a possible relationship between 5-HT and psychiatric disease was spurred by the observations that hallucinogens such as LSD and psilocybin inhibit the actions of 5-HT on smooth muscle preparations (Gaddum, J. H. and Hameed, K. A., *Br J Pharmacol* 9, 240–248 (1954)). This observation lead to the hypothesis that brain 5-HT activity might be altered in psychiatric disorders (Wooley, D. W. and Shaw, E., *Proc Natl Acad Sci USA* 40, 228–231 (1954); Gaddum, J. H. and Picarelli, Z. P., *Br J Pharmacol* 12, 323–328 (1957)). This hypothesis was strengthened by the introduction of tricyclic antidepressants and monoamine oxidase inhibitors for the treatment of major depression and the observation that those drugs affected noradrenaline and 5-HT metabolism. Today, drugs acting on the serotoninergic system have been proved to be effective in the pharmacotherapy of psychiatric diseases such as depression, schizophrenia, obsessive-compulsive disorder, panic disorder, generalized anxiety disorder and social phobia as well as migraine, vomiting induced by cancer chemotherapy and gastric motility disorders.

Serotonin receptors represent a very large and diverse family of neurotransmitter receptors. To date thirteen 5-HT receptor proteins coupled to G proteins plus one ligand-gated ion channel receptor (5-HT3) have been described in mammals. This receptor diversity is thought to reflect serotonin's ancient origin as a neurotransmitter and a hormone as well as the many different roles of 5-HT in mammals. The 5-HT receptors have been classified into seven subfamilies or groups according to their different ligand-binding affinity profiles, molecular structure and intracellular transduction mechanisms (Hoyer, D. et al., *Pharmacol. Rev.* 46, 157–203 (1994)).

Adrenergic GPCRs

The adrenergic receptors comprise one of the largest and most extensively characterized families within the G-protein coupled receptor "superfamily". This superfamily includes not only adrenergic receptors, but also muscarinic, cholinergic, dopaminergic, serotonergic, and histaminergic receptors. Numerous peptide receptors include glucagon, somatostatin, and vasopressin receptors, as well as sensory receptors for vision (rhodopsin), taste, and olfaction, also belong to this growing family. Despite the diversity of signalling molecules, G-protein coupled receptors all possess a similar overall primary structure, characterized by 7 putative membrane-spanning .alpha. helices (Probst et al., 1992). In the most basic sense, the adrenergic receptors are the physiological sites of action of the catecholamines, epinephrine and norepinephrine. Adrenergic receptors were initially classified as either .alpha. or .beta. by Ahlquist, who demonstrated that the order of potency for a series of agonists to evoke a physiological response was distinctly different at the 2 receptor subtypes (Ahlquist, 1948). Functionally, .alpha. adrenergic receptors were shown to control vasoconstriction, pupil dilation and uterine inhibition, while .beta. adrenergic receptors were implicated in vasorelaxation, myocardial stimulation and bronchodilation (Regan et al., 1990). Eventually, pharmacologists realized that these responses resulted from activation of several distinct adrenergic receptor subtypes .beta. adrenergic receptors in the heart were defined as .beta..sub.1, while those in the lung and vasculature were termed .beta..sub.2 (Lands et al., 1967).

.alpha. Adrenergic receptors, meanwhile, were first classified based on their anatomical location, as either pre or post-synaptic (.alpha..sub.2 and alpha..sub. 1, respectively) (Langer et al., 1974). This classification scheme was confounded, however, by the presence of .alpha..sub.2 receptors in distinctly non-synaptic locations, such as platelets (Berthelsen and Pettinger, 1977). With the development of radioligand binding techniques, .alpha. adrenergic receptors could be distinguished pharmacologically based on their affinities for the antagonists prazosin or yohimbine (Stark, 1981). Definitive evidence for adrenergic receptor subtypes, however, awaited purification and molecular cloning of adrenergic receptor subtypes. In 1986, the genes for the hamster .beta..sub.2 (Dickson et al., 1986) and turkey .beta..sub.1 adrenergic receptors (Yarden et al., 1986) were cloned and sequenced. Hydropathy analysis revealed that these proteins contain 7 hydrophobic domains similar to rhodopsin, the receptor for light. Since that time the adrenergic receptor family has expanded to include 3 subtypes of .beta. receptors (Emorine et al., 1989), 3 subtypes of .alpha..sub.1 receptors (Schwinn et al., 1990), and 3 distinct types of .beta..sub.2 receptors (Lomasney et al., 1990).

The cloning, sequencing and expression of alpha receptor subtypes from animal tissues has led to the subclassification of the alpha 1 receptors into alpha 1d (formerly known as alpha 1a or 1a/1d), alpha 1b and alpha 1a (formerly known as alpha 1c) subtypes. Each alpha 1 receptor subtype exhibits its own pharmacologic and tissue specificities. The designation "alpha 1a" is the appellation recently approved by the IUPHAR Nomenclature Committee for the previously designated "alpha 1c" cloned subtype as outlined in the 1995 Receptor and Ion Channel Nomenclature Supplement (Watson and Girdlestone, 1995). The designation alpha la is used throughout this application to refer to this subtype. At the same time, the receptor formerly designated alpha 1a was renamed alpha 1d. The new nomenclature is used throughout this application. Stable cell lines expressing these alpha 1 receptor subtypes are referred to herein; however, these cell lines were deposited with the American Type Culture Collection (ATCC) under the old nomenclature. For a review of the classification of alpha 1 adrenoceptor subtypes, see, Martin C. Michel, et al., Naunyn-Schmiedeberg's Arch. Pharmacol. (1995) 352:1–10.

The differences in the alpha adrenergic receptor subtypes have relevance in pathophysiologic conditions. Benign prostatic hyperplasia, also known as benign prostatic hypertrophy or BPH, is an illness typically affecting men over fifty years of age, increasing in severity with increasing age. The symptoms of the condition include, but are not limited to, increased difficulty in urination and sexual dysfunction. These symptoms are induced by enlargement, or hyperplasia, of the prostate gland. As the prostate increases in size, it impinges on free-flow of fluids through the male urethra.

Concommitantly, the increased noradrenergic innervation of the enlarged prostate leads to an increased adrenergic tone of the bladder neck and urethra, further restricting the flow of urine through the urethra.

The .alpha..sub.2 receptors appear to have diverged rather early from either .beta. or .alpha..sub.1 receptors. The .alpha..sub.2 receptors have been broken down into 3 molecularly distinct subtypes termed .alpha..sub.2 C2, .alpha..sub.2 C4, and .alpha..sub.2 C10 based on their chromosomal location. These subtypes appear to correspond to the respectively (Bylund et al., 1992). While all the receptors of the adrenergic type are recognized by epinephrine, they are pharmacologically distinct and are encoded by separate genes. These receptors are generally coupled to different second messenger pathways that are linked through G-proteins. Among the adrenergic receptors, .beta..sub. 1 and .beta..sub.2 receptors activate the adenylate cyclase, .alpha..sub.2 receptors inhibit adenylate cyclase and .alpha..sub.1 receptors activate phospholipase C pathways, stimulating breakdown of polyphosphoinositides (Chung, F. Z. et al., J. Biol. Chem., 263:4052 (1988)). .alpha..sub.1 and .alpha..sub.2 adrenergic receptors differ in their cell activity for drugs.

Issued US patent that disclose the utility of members of this family of proteins include, but are not limited to, U.S. Pat. No. 6,063,785 Phthalimido arylpiperazines useful in the treatment of benign prostatic hyperplasia; U.S. Pat. No. 6,060,492 Selective .beta.3 adrenergic agonists; U.S. Pat. No. 6,057,350 Alpha la adrenergic receptor antagonists; U.S. Pat. No. 6,046,192 Phenylethanolaminotetralincarboxamide derivatives; U.S. Pat. No. 6,046,183 Method of synergistic treatment for benign prostatic hyperplasia; U.S. Pat. No. 6,043,253 Fused piperidine substituted arylsulfonamides as .beta.3-agonists; U.S. Pat. No. 6,043,224 Compositions and methods for treatment of neurological disorders and neurodegenerative diseases; U.S. Pat. No. 6,037,354 Alpha 1a adrenergic receptor antagonists; U.S. Pat. No. 6,034,106 Oxadiazole benzenesulfonamides as selective .beta..sub.3 Agonist for the treatment of Diabetes and Obesity; U.S. Pat. No. 6,011,048 Thiazole benzenesulfonamides as .beta.3 agonists for treatment of diabetes and obesity; U.S. Pat. Nos. 6,008,361 5,994,506 Adrenergic receptor; U.S. Pat. No. 5,994,294 Nitrosated and nitrosylated .alpha.-adrenergic receptor antagonist compounds, compositions and their uses; U.S. Pat. No. 5,990,128 .alpha..sub.1C specific compounds to treat benign prostatic hyperplasia; U.S. Pat. No. 5,977,154 Selective .beta.3 adrenergic agonist; U.S. Pat. No. 5,977,115 Alpha 1a adrenergic receptor antagonists; U.S. Pat. No. 5,939,443 Selective .beta.3 adrenergic agonists; U.S. Pat. No. 5,932,538 Nitrosated and nitrosylated .alpha.-adrenergic receptor antagonist compounds, compositions and their uses; U.S. Pat. No. 5,922,722 Alpha 1a adrenergic receptor antagonists 26 U.S. Pat. Nos. 5,908,830 and 5,861,309 DNA endoding human alpha 1 adrenergic receptors.

Purinergic GPCRs

Purinoceptor P2Y1

P2 purinoceptors have been broadly classified as P2X receptors which are ATP-gated channels; P2Y receptors, a family of G protein-coupled receptors, and P2Z receptors, which mediate nonselective pores in mast cells. Numerous subtypes have been identified for each of the P2 receptor classes. P2Y receptors are characterized by their selective responsiveness towards ATP and its analogs. Some respond also to UTP. Based on the recommendation for nomenclature of P2 purinoceptors, the P2Y purinoceptors were numbered in the order of cloning. P2Y1, P2Y2 and P2Y3 have been cloned from a variety of species. P2Y1 responds to both ADP and ATP. Analysis of P2Y receptor subtype expression in human bone and 2 osteoblastic cell lines by RT-PCR showed that all known human P2Y receptor subtypes were expressed: P2Y1, P2Y2, P2Y4, P2Y6, and P2Y7 (Maier (Maier et al. 1997). In contrast, analysis of brain-derived cell lines suggested that a selective expression of P2Y receptor subtypes occurs in brain tissue.

Leon et al. generated P2Y1-null mice to define the physiologic role of the P2Y1 receptor. (J. Clin. Invest. 104: 1731–1737(1999)) These mice were viable with no apparent abnormalities affecting their development, survival, reproduction, or morphology of platelets, and the platelet count in these animals was identical to that of wildtype mice. However, platelets from P2Y 1-deficient mice were unable to aggregate in response to usual concentrations of ADP and displayed impaired aggregation to other agonists, while high concentrations of ADP induced platelet aggregation without shape change. In addition, ADP-induced inhibition of adenylyl cyclase still occurred, demonstrating the existence of an ADP receptor distinct from P2Y1. P2Y1-null mice had no spontaneous bleeding tendency but were resistant to thromboembolism induced by intravenous injection of ADP or collagen and adrenaline. Hence, the P2Y1 receptor plays an essential role in thrombotic states and represents a potential target for antithrombotic drugs. Somers et al. mapped the P2RY1 gene between flanking markers D3S1279 and D3S1280 at a position 173 to 174 cM from the most telomeric markers on the short arm of chromosome 3. (Genomics 44: 127–130 (1997)).

Purinoceptor P2Y2

The chloride ion secretory pathway that is defective in cystic fibrosis (CF) can be bypassed by an alternative pathway for chloride ion transport that is activated by extracellular nucleotides. Accordingly, the P2 receptor that mediates this effect is a therapeutic target for improving chloride secretion in CF patients. Parr et al. reported the sequence and functional expression of a cDNA cloned from human airway epithelial cells that encodes a protein with properties of a P2Y nucleotide receptor. (Proc. Nat. Acad. Sci. 91: 3275–3279(1994)) The human P2RY2 gene was mapped to chromosome 11q13.5–q14.1.

Purinoceptor P2RY4

The P2RY4 receptor appears to be activated specifically by UTP and UDP, but not by ATP and ADP. Activation of this uridine nucleotide receptor resulted in increased inositol phosphate formation and calcium mobilization. The UNR gene is located on chromosome Xq13.

Purinoceptor P2Y6

Somers et al. mapped the P2RY6 gene to 11q13.5, between polymorphic markers D11S1314 and D11S916, and P2RY2 maps within less than 4 cM of P2RY6. (Genomics 44: 127–130 (1997)) This was the first chromosomal clustering of this gene family to be described.

Adenine and uridine nucleotides, in addition to their well established role in intracellular energy metabolism, phosphorylation, and nucleic acid synthesis, also are important extracellular signaling molecules. P2Y metabotropic receptors are GPCRs that mediate the effects of extracellular nucleotides to regulate a wide variety of physiological processes. At least ten subfamilies of P2Y receptors have been identified. These receptor subfamilies differ greatly in their sequences and in their nucleotide agonist selectivities and efficacies.

It has been demonstrated that the P2Y1 receptors are strongly expressed in the brain, but the P2Y2, P2Y4 and P2Y6 receptors are also present. The localisation of one or more of these subtypes on neurons, on glia cells, on brain vasculature or on ventricle ependimal cells was found by in situ mRNA hybridisation and studies on those cells in culture. The P2Y1 receptors are prominent on neurons. The coupling of certain P2Y receptor subtypes to N-type Ca2+ channels or to particular K+ channels was also demonstrated.

It has also been demonstrated that several P2Y receptors mediate potent growth stimulatory effects on smooth muscle cells by stimulating intracellular pathways including Gq-proteins, protein kinase C and tyrosine phosphorylation, leading to increased immediate early gene expression, cell number, DNA and protein synthesis. It has been further demonstrated that P2Y regulation plays a nitogenic role in response to the development of artherosclerosis.

It has further been demonstrated that P2Y receptors play a critical role in cystic fibrosis. The volume and composition of the liquid that lines the airway surface is modulated by active transport of ions across the airway epithelium. This in turn is regulated both by autonomic agonists acting on basolateral receptors and by agonists acting on luminal receptors. Specifically, extracellular nucleotides present in the airway surface liquid act on luminal P2Y receptors to control both Cl− secretion and Na+ absorption. Since nucleotides are released in a regulated manner from airway epithelial cells, it is likely that their control over airway ion transport forms part of an autocrine regulatory system localised to the luminal surface of airway epithelia. In addition to this physiological role, P2Y receptor agonists have the potential to be of crucial benefit in the treatment of CF, a disorder of epithelial ion transport. The airways of people with CF have defective Cl− secretion and abnormally high rates of Na+ absorption. Since P2Y receptor agonists can regulate both these ion transport pathways they have the potential to pharmacologically bypass the ion transport defects in CF.

The present invention has a substantial similarity to purinergic receptor P2X-like 1 (purinoceptor P2X6). P2X-like purinergic receptor is an orphan receptor, and is known to be expressed in skeletal muscle. P2X6 belongs to the ATP-gated ion channel family. The rat P2X6 nucleotide sequence encodes a 379 amino acid protein that conserves all the structural features of previously cloned P2X receptors, including the two putative transmembrane domains predicted by hydrophobicity plots. In addition, P2XM, a subfamily of P2X-like purinergic receptor was localized to chromosomal band 22q11, where frequent loss of heterozygosity has been observed in rhabdoid tumors. This protein was implicated to play a significant role in the proliferation and/or differentiation of skeletal muscle cells and that its altered expression may be involved in the development of some sarcomas. For a review related to P2X-like purinergic receptor, see Spener et al., Mol. Cell. Biochem. 98 (1–2), 57–68 (1990); Peeters et al., Biochem. J. 276 (Pt 1), 203–207 (1991); Zanotti et al., J. Biol. Chem. 267 (26), 18541–18550 (1992); Troxler et al., Hum. Genet. 92 (6), 563–566 (1993); Huynh et al., Cancer Res. 55 (11), 2225–2231 (1995); Phelan et al., Genomics 34 (1), 63–68 (1996); Urano et al., Cancer Res 1997 August 1; 57(15): 3281–7; Soto et al., Biochem Biophys Res Commun 14; Jun. 14, 223(2): 456–60.

GPCRs, particularly members of the P2X-like purinergic receptor subfamily, are a major target for drug action and development. Accordingly, it is valuable to the field of pharmaceutical development to identify and characterize previously unknown GPCRs. The present invention advances the state of the art by providing a previously unidentified human GPCR.

SUMMARY OF THE INVENTION

The present invention is based in part on the identification of nucleic acid sequences that encode amino acid sequences of human GPCR peptides and proteins that are related to the P2X-like purinergic receptor subfamily, allelic variants thereof and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents.

The proteins of the present inventions are GPCRs that participate in signaling pathways mediated by the P2X-like purinergic receptor subfamily in cells that express these proteins. Experimental data as provided in FIG. 1 indicates expression in the anaplastic oligodendroglioma(brain), chronic lyphocytic leukemia, carcinoid lung, large cell lung carcinoma and colon and whole brain. As used herein, a "signaling pathway" refers to the modulation (e.g., stimulation or inhibition) of a cellular function/activity upon the binding of a ligand to the GPCR protein. Examples of such functions include mobilization of intracellular molecules that participate in a signal transduction pathway, e.g., phosphatidylinositol 4,5-bisphosphate ($PIP_2$), inositol 1,4,5-triphosphate ($IP_3$) and adenylate cyclase; polarization of the plasma membrane; production or secretion of molecules; alteration in the structure of a cellular component; cell proliferation, e.g., synthesis of DNA; cell migration; cell differentiation; and cell survival The response mediated by the receptor protein depends on the type of cell it is expressed on. Some information regarding the types of cells that express other members of the subfamily of GPCRs of the present invention is already known in the art (see references cited in Background and information regarding closest homologous protein provided in FIG. 2; Experimental data as provided in FIG. 1 indicates expression in the anaplastic oligodendroglioma(brain), chronic lyphocytic leukemia, carcinoid lung, large cell lung carcinoma and colon and whole brain. For example, in some cells, binding of a ligand to the receptor protein may stimulate an activity such as release of compounds, gating of a channel, cellular adhesion, migration, differentiation, etc., through phosphatidylinositol or cyclic AMP metabolism and turnover while in other cells, the binding of the ligand will produce a different result. Regardless of the cellular activity/response modulated by the particular GPCR of the present invention, a skilled artisan will clearly know that the receptor protein is a GPCR and interacts with G proteins to produce one or more secondary signals, in a variety of intracellular signal transduction pathways, e.g., through phosphatidylinositol or cyclic AMP metabolism and turnover, in a cell thus participating in a biological process in the cells or tissues that express the GPCR. Experimental data as provided in FIG. 1 indicates that GPCR proteins of the present invention are expressed in the anaplastic oligodendroglioma(brain), chronic lyphocytic leukemia, carcinoid lung, large cell lung carcinoma and colon detected by a virtual northern blot. In addition, PCR-based tissue screening panel indicates expression in whole brain.

As used herein, "phosphatidylinositol turnover and metabolism" refers to the molecules involved in the turnover and metabolism ofphosphatidylinositol 4,5-bisphosphate (PIP$_2$) as well as to the activities of these molecules. PIP$_2$ is a phospholipid found in the cytosolic leaflet of the plasma membrane. Binding of ligand to the receptor activates, in some cells, the plasma-membrane enzyme phospholipase C that in turn can hydrolyze PIP$_2$ to produce 1,2-diacylglycerol (DAG) and inositol 1,4,5-triphosphate (IP$_3$). Once formed IP$_3$ can diffuse to the endoplasmic reticulum surface where it can bind an IP$_3$ receptor, e.g., a calcium channel protein containing an IP$_3$ binding site. IP$_3$ binding can induce opening of the channel, allowing calcium ions to be released into the cytoplasm. IP$_3$ can also be phosphorylated by a specific kinase to form inositol 1,3,4,5-tetraphosphate (IP$_4$), a molecule that can cause calcium entry into the cytoplasm from the extracellular medium. IP$_3$ and IP$_4$ can subsequently be hydrolyzed very rapidly to the inactive products inositol 1,4-biphosphate (IP$_2$) and inositol 1,3,4-triphosphate, respectively. These inactive products can be recycled by the cell to synthesize PIP$_2$. The other second messenger produced by the hydrolysis of PIP$_2$, namely 1,2-diacylglycerol (DAG), remains in the cell membrane where it can serve to activate the enzyme protein kinase C. Protein kinase C is usually found soluble in the cytoplasm of the cell, but upon an increase in the intracellular calcium concentration, this enzyme can move to the plasma membrane where it can be activated by DAG. The activation of protein kinase C in different cells results in various cellular responses such as the phosphorylation of glycogen synthase, or the phosphorylation of various transcription factors, e.g., NF-kB. The language "phosphatidylinositol activity", as used herein, refers to an activity of PIP$_2$ or one of its metabolites.

Another signaling pathway in which the receptor may participate is the cAMP turnover pathway. As used herein, "cyclic AMP turnover and metabolism" refers to the molecules involved in the turnover and metabolism of cyclic AMP (cAMP) as well as to the activities of these molecules. Cyclic AMP is a second messenger produced in response to ligand-induced stimulation of certain G protein coupled receptors. In the cAMP signaling pathway, binding of a ligand to a GPCR can lead to the activation of the enzyme adenyl cyclase, which catalyzes the synthesis of cAMP. The newly synthesized cAMP can in turn activate a cAMP-dependent protein kinase. This activated kinase can phosphorylate a voltage-gated potassium channel protein, or an associated protein, and lead to the inability of the potassium channel to open during an action potential. The inability of the potassium channel to open results in a decrease in the outward flow of potassium, which normally repolarizes the membrane of a neuron, leading to prolonged membrane depolarization.

By targeting an agent to modulate a GPCR, the signaling activity and biological process mediated by the receptor can be agonized or antagonized in specific cells and tissues. Experimental data as provided in FIG. 1 indicates expression in the anaplastic oligodendroglioma(brain), chronic lyphocytic leukemia, carcinoid lung, large cell lung carcinoma and colon and whole brain. Such agonism and antagonism serves as a basis for modulating a biological activity in a therapeutic context (mammalian therapy) or toxic context (anti-cell therapy, e.g. anti-cancer agent).

DESCRIPTION OF THE FIGURE SHEETS

FIG. 1 provides the nucleotide sequence of a cDNA molecule or transcript sequence that encodes the GPCR of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in the anaplastic oligodendroglioma (brain), chronic lyphocytic leukemia, carcinoid lung, large cell lung carcinoma and colon and whole brain.

FIG. 2 provides the predicted amino acid sequence of the GPCR of the present invention. (SEQ ID NO:2) In addition structure and functional information such as protein family, function, and modification sites is provided where available, allowing one to readily determine specific uses of inventions based on this molecular sequence.

FIG. 3 provides genomic sequences that span the gene encoding the GPCR protein of the present invention. (SEQ ID NO:3) In addition structure and functional information, such as intron/exon structure, promoter location, etc., is provided where available, allowing one to readily determine specific uses of inventions based on this molecular sequence. As illustrated in FIG. 3, SNPs, were identified at 21 different nucleotide positions.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a GPCR protein or part of a GPCR protein, that are related to the P2X-like purinergic receptor subfamily. Utilizing these sequences, additional genomic sequences were assembled and transcript and/or cDNA sequences were isolated and characterized. Based on this analysis, the present invention provides amino acid sequences of human GPCR peptides and proteins that are related to the P2X-like purinergic receptor subfamily, nucleic acid sequences in the form of transcript sequences, cDNA sequences and/or genomic sequences that encode these GPCR peptides and proteins, nucleic acid variation (allelic information), tissue distribution of expression, and information about the closest art known protein/peptide/domain that has structural or sequence homology to the GPCR of the present invention. In addition to being previously unknown, the peptides that are provided in the present invention are selected based on their ability to be used for the development of commercially important products and services. Specifically, the present peptides are selected based on homology and/or structural relatedness to known GPCR proteins of the P2X-like purinergic receptor subfamily and the expression pattern observed. Experimental data as provided in FIG. 1 indicates expression in the anaplastic oligodendroglioma(brain), chronic lyphocytic leukemia, carcinoid lung, large cell lung carcinoma and colon and whole brain. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known P2X-like purinergic receptor family or subfamily of GPCR proteins.

SPECIFIC EMBODIMENTS

Peptide Molecules

The present invention provides nucleic acid sequences that encode protein molecules that have been identified as being members of the GPCR family of proteins and are related to the P2X-like purinergic receptor subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the GPCR peptides of the present invention, GPCR peptides, or peptides/proteins of the present invention.

The present invention provides isolated peptide and protein molecules that consist of, consist essentially of, or comprise the amino acid sequences of the GPCR peptides disclosed in FIG. 2, (encoded by the nucleic acid molecule shown in FIG. 1, transcript/cDNA sequence, or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the GPCR peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated GPCR peptide can be purified from cells that naturally express it, purified from cells that have been altered to express it (recombinant), or synthesized using known protein synthesis methods. Experimental data as provided in FIG. 1 indicates expression in the anaplastic oligodendroglioma(brain), chronic lyphocytic leukemia, carcinoid lung, large cell lung carcinoma and colon and whole brain. For example, a nucleic acid molecule encoding the GPCR peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the GPCR peptides of the present invention are the naturally occurring mature proteins. A brief description of how various types of these proteins can be made/isolated is provided below.

The GPCR peptides of the present invention can be attached to heterologous sequences to form chimeric or fusion proteins. Such chimeric and fusion proteins comprise a GPCR peptide operatively linked to a heterologous protein having an amino acid sequence not substantially homologous to the GPCR peptide. "Operatively linked" indicates that the GPCR peptide and the heterologous protein are fused in-frame. The heterologous protein can be fused to the N-terminus or C-terminus of the GPCR peptide.

In some uses, the fusion protein does not affect the activity of the GPCR peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant GPCR peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A GPCR peptide-encoding nucleic acid can be cloned into such an expression vector such that the fusion moiety is linked in-frame to the GPCR peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the GPCR peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, 40%, 50%, 60%, 70%, 80%, or 90% or more of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part 1*, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package, using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the GPCR peptides of the present invention as well as being encoded by the same genetic locus as the GPCR peptide provided herein. As indicated by the data presented in FIG. 3, the map position was determined to be on chromosome 22 by ePCR.

Allelic variants of a GPCR peptide can readily be identified as being a human protein having a high degree (significant) of sequence homology/identity to at least a portion of the GPCR peptide as well as being encoded by the same genetic locus as the GPCR peptide provided herein. Genetic locus can readily be determined based on the genomic information provided in FIG. 3, such as the genomic sequence mapped to the reference human. As indicated by the data presented in FIG. 3, the map position was determined to be on chromosome 22 by ePCR. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a GPCR peptide encoding nucleic acid molecule under stringent conditions as more fully described below.

FIG. 3 provides information on SNPs that have been found in the gene encoding the GPCR protein of the present invention. SNPs were identified at 21 different nucleotide positions in exon, introns and regions 5' and 3' of the ORF. Such SNPs in introns and outside the ORF may affect control/regulatory elements.

Paralogs of a GPCR peptide can readily be identified as having some degree of significant sequence homology/identity to at least a portion of the GPCR peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a GPCR peptide encoding nucleic acid molecule under moderate to stringent conditions as more fully described below.

Orthologs of a GPCR peptide can readily be identified as having some degree of significant sequence homology/identity to at least a portion of the GPCR peptide as well as being encoded by a gene from another organism. Preferred orthologs will be isolated from mammals, preferably primates, for the development of human therapeutic targets and agents. Such orthologs will be encoded by a nucleic acid sequence that will hybridize to a GPCR peptide encoding nucleic acid molecule under moderate to stringent conditions, as more fully described below, depending on the degree of relatedness of the two organisms yielding the proteins.

Non-naturally occurring variants of the GPCR peptides of the present invention can readily be generated using recombinant techniques. Such variants include, but are not limited to deletions, additions and substitutions in the amino acid sequence of the GPCR peptide. For example, one class of substitutions are conserved amino acid substitution. Such substitutions are those that substitute a given amino acid in a GPCR peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant GPCR peptides can be fully functional or can lack function in one or more activities, e.g. ability to bind ligand, ability to bind G-protein, ability to mediate signaling, etc. Fully functional variants typically contain only conservative variation or variation in non-critical residues or in non-critical regions. FIG. 2 provides the result of protein analysis that identifies critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as ligand/effector molecule binding or in assays such as an in vitro proliferative activity. Sites that are critical for ligand-receptor binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the GPCR peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a GPCR peptide. Such fragments can be chosen based on the ability to retain one or more of the biological activities of the GPCR peptide or could be chosen for the ability to perform a function, e.g. ability to bind ligand or effector molecule or act as an immunogen. Particularly important fragments are biologically active fragments, peptides which are, for example, about 8 or more amino acids in length. Such fragments will typically comprise a domain or motif of the GPCR peptide, e.g., active site, a G-protein binding site, a transmembrane domain or a ligand-binding domain. Further, possible fragments include, but are not limited to, domain or motif containing fragments, soluble peptide fragments, and fragments containing immunogenic structures. Predicted domains and functional sites are readily identifiable by computer programs well-known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in GPCR peptides are described in basic texts, detailed monographs, and the research literature, and they are well known to those of skill in the art(some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well-known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

Accordingly, the GPCR peptides of the present invention also encompass derivatives or analogs in which a substituted amino acid residue is not one encoded by the genetic code, in which a substituent group is included, in which the mature GPCR peptide is fused with another compound, such as a compound to increase the half-life of the GPCR peptide (for example, polyethylene glycol), or in which the additional amino acids are fused to the mature GPCR peptide, such as a leader or secretory sequence or a sequence for purification of the mature GPCR peptide or a pro-protein sequence.

Protein/Peptide Uses

The proteins of the present invention can be used in substantial and specific assays related to the functional information provided in the Figures and Back Ground Section; to raise antibodies or to elicit another immune response; as a reagent (including the labeled reagent) in assays designed to quantitatively determine levels of the protein (or its binding partner or receptor) in biological fluids; and as markers for tissues in which the corresponding protein is preferentially expressed (either constitutively or at a particular stage of tissue differentiation or development or in a disease state). Where the protein binds or potentially binds to another protein (such as, for example, in a receptor-ligand interaction), the protein can be used to identify the binding partner so as to develop a system to identify inhibitors of the binding interaction. Any or all of these research utilities are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, GPCRs isolated from humans and their human/mammalian orthologs serve as targets for identifying agents for use in mammalian therapeutic applications, e.g. a human drug, particularly in modulating a biological or pathological response in a cell or tissue that expresses the GPCR. Experimental data as provided in FIG. 1 indicates that GPCR proteins of the present invention are expressed in the anaplastic oligodendroglioma (brain), chronic lyphocytic leukemia, carcinoid lung, large cell lung carcinoma and colon detected by a virtual northern blot. In addition, PCR-based tissue screening panel indicates expression in whole brain. Approximately 70% of all pharmaceutical agents modulate the activity of a GPCR. A combination of the invertebrate and mammalian ortholog can be used in selective screening methods to find agents specific for invertebrates. The structural and functional information provided in the Background and Figures provide specific and substantial uses for the molecules of the present invention, particularly in combination with the expression information provided in FIG. 1. Experimental data as provided in FIG. 1 indicates expression in the anaplastic oligodendroglioma(brain), chronic lyphocytic leukemia, carcinoid lung, large cell lung carcinoma and colon and whole brain. Such uses can readily be determined using the information provided herein, that known in the art and routine experimentation.

The proteins of the present invention (including variants and fragments that may have been disclosed prior to the present invention) are useful for biological assays related to GPCRs that are related to members of the P2X-like purinergic receptor subfamily. Such assays involve any of the known GPCR functions or activities or properties useful for diagnosis and treatment of GPCR-related conditions that are specific for the subfamily of GPCRs that the one of the present invention belongs to, particularly in cells and tissues that express this receptor. Experimental data as provided in FIG. 1 indicates that GPCR proteins of the present invention are expressed in the anaplastic oligodendroglioma(brain), chronic lyphocytic leukemia, carcinoid lung, large cell lung carcinoma and colon detected by a virtual northern blot. In addition, PCR-based tissue screening panel indicates expression in whole brain.

The proteins of the present invention are also useful in drug screening assays, in cell-based or cell-free systems. Cell-based systems can be native, i.e., cells that normally express the receptor protein, as a biopsy or expanded in cell culture. Experimental data as provided in FIG. 1 indicates expression in the anaplastic oligodendroglioma(brain), chronic lyphocytic leukemia, carcinoid lung, large cell lung carcinoma and colon and whole brain. In an alternate embodiment, cell-based assays involve recombinant host cells expressing the receptor protein.

The polypeptides can be used to identify compounds that modulate receptor activity of the protein in its natural state, or an altered form that causes a specific disease or pathology associated with the receptor. Both the GPCRs of the present invention and appropriate variants and fragments can be used in high-throughput screens to assay candidate compounds for the ability to bind to the receptor. These compounds can be further screened against a functional receptor to determine the effect of the compound on the receptor activity. Further, these compounds can be tested in animal or invertebrate systems to determine activity/effectiveness. Compounds can be identified that activate (agonist) or inactivate (antagonist) the receptor to a desired degree.

Further, the proteins of the present invention can be used to screen a compound for the ability to stimulate or inhibit interaction between the receptor protein and a molecule that normally interacts with the receptor protein, e.g. a ligand or a component of the signal pathway that the receptor protein normally interacts (for example, a G-protein or other interactor involved in cAMP or phosphatidylinositol turnover and/or adenylate cyclase, or phospholipase C activation). Such assays typically include the steps of combining the receptor protein with a candidate compound under conditions that allow the receptor protein, or fragment, to interact with the target molecule, and to detect the formation of a complex between the protein and the target or to detect the biochemical consequence of the interaction with the receptor protein and the target, such as any of the associated effects of signal transduction such as G-protein phosphorylation, cAMP or phosphatidylinositol turnover, and adenylate cyclase or phospholipase C activation.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for ligand binding. Other candidate compounds include mutant receptors or appropriate fragments containing mutations that affect receptor function and thus compete for ligand. Accordingly, a fragment that competes for ligand, for example with a higher affinity, or a fragment that binds ligand but does not allow release, is encompassed by the invention.

The invention further includes other end point assays to identify compounds that modulate (stimulate or inhibit) receptor activity. The assays typically involve an assay of events in the signal transduction pathway that indicate receptor activity. Thus, a cellular process such as proliferation, the expression of genes that are up- or down-regulated in response to the receptor protein dependent signal cascade, can be assayed. In one embodiment, the regulatory region of such genes can be operably linked to a marker that is easily detectable, such as luciferase.

Any of the biological or biochemical functions mediated by the receptor can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the receptor can be assayed. Experimental data as provided in FIG. 1 indicates that GPCR proteins of the present invention are expressed in the anaplastic oligodendroglioma(brain), chronic lyphocytic leukemia, carcinoid lung, large cell lung carcinoma and colon detected by a virtual northern blot. In addition, PCR-based tissue screening panel indicates expression in whole brain.

Binding and/or activating compounds can also be screened by using chimeric receptor proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a G-protein-binding region can be used that interacts with a different G-protein then that which is recognized by the native receptor. Accordingly, a different set of signal transduction components is available as an end-point assay for activation. Alternatively, the entire transmembrane portion or subregions (such as transmembrane segments or intracellular or extracellular loops) can be replaced with the entire transmembrane portion or subregions specific to a host cell that is different from the host cell from which the amino terminal extracellular domain and/or the G-protein-binding region are derived. This allows for assays to be performed in other than the specific host cell from which the receptor is derived. Alternatively, the amino terminal extracellular domain (and/or other ligand-binding regions) could be replaced by a domain (and/or other binding region) binding a different ligand, thus, providing an assay for test compounds that interact with the heterologous amino terminal extracellular domain (or region) but still cause signal transduction. Finally, activation can be detected by a reporter gene containing an easily detectable coding region operably linked to a transcriptional regulatory sequence that is part of the native signal transduction pathway.

The proteins of the present invention are also useful in competition binding assays in methods designed to discover compounds that interact with the receptor. Thus, a compound is exposed to a receptor polypeptide under conditions that allow the compound to bind or to otherwise interact with the polypeptide (Hodgson, Bio/technology, September 10, 1992, (9);973–80). Soluble receptor polypeptide is also added to the mixture. If the test compound interacts with the soluble receptor polypeptide, it decreases the amount of complex formed or activity from the receptor target. This type of assay is particularly useful in cases in which compounds are sought that interact with specific regions of the receptor. Thus, the soluble polypeptide that competes with the target receptor region is designed to contain peptide sequences corresponding to the region of interest.

To perform cell free drug screening assays, it is sometimes desirable to inmobilize either the receptor protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of receptor-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a receptor-binding protein and a candidate compound are incubated in the receptor protein-presenting wells and the amount of complex trapped in the well can be quantitated. Methods for detecting such complexes, in addition to those described above for the GST-immobilized complexes, include immunodetection of complexes using antibodies reactive with the receptor protein target molecule, or which are reactive with receptor protein and compete with the target molecule, as well as enzyme-linked assays which rely on detecting an enzymatic activity associated with the target molecule.

Agents that modulate one of the GPCRs of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of receptor protein activity identified according to these drug screening assays can be used to treat a subject with a disorder mediated by the receptor pathway, by treating cells or tissues that express the GPCR. Experimental data as provided in FIG. 1 indicates expression in the anaplastic oligodendroglioma(brain), chronic lyphocytic leukemia, carcinoid lung, large cell lung carcinoma and colon and whole brain. These methods of treatment include the steps of administering a modulator of the GPCR's activity in a pharmaceutical composition to a subject in need of such treatment, the modulator being identified as described herein.

In yet another aspect of the invention, the GPCR proteins can be used as "bait proteins" in a two-hybrid assay or three-hybrid assay (see, e.g., U.S. Pat. No. 5,283,317; Zervos et al. (1993) Cell 72:223–232; Madura et al. (1993) J. Biol. Chem. 268:12046–12054; Bartel et al. (1993) Biotechniques 14:920–924; Iwabuchi et al. (1993) Oncogene 8:1693–1696; and Brent WO94/10300), to identify other proteins, which bind to or interact with the GPCR and are involved in GPCR activity. Such GPCR-binding proteins are also likely to be involved in the propagation of signals by the GPCR proteins or GPCR targets as, for example, downstream elements of a GPCR-mediated signaling pathway. Alternatively, such GPCR-binding proteins are likely to be GPCR inhibitors.

The two-hybrid system is based on the modular nature of most transcription factors, which consist of separable DNA-binding and activation domains. Briefly, the assay utilizes two different DNA constructs. In one construct, the gene that codes for a GPCR protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a GPCR-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the GPCR protein.

This invention further pertains to novel agents identified by the above-described screening assays. Accordingly, it is within the scope of this invention to further use an agent identified as described herein in an appropriate animal model. For example, an agent identified as described herein (e.g., a GPCR modulating agent, an antisense GPCR nucleic acid molecule, a GPCR-specific antibody, or a GPCR-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The GPCR proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in the anaplastic oligodendroglioma(brain), chronic lyphocytic leukemia, carcinoid lung, large cell lung carcinoma and colon and whole brain. The method involves contacting a biological sample with a compound capable of interacting with the receptor protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered receptor activity in cell-based or cell-free assay, alteration in ligand or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (Clin. Exp. Pharmacol. Physiol. 23(10–11):983–985 (1996)), and Linder, M. W. (Clin. Chem. 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype.

The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the receptor protein in which one or more of the receptor functions in one population is different from those in another population. The peptides thus allow a target to ascertain a genetic predisposition that can affect treatment modality. Thus, in a ligand-based treatment, polymorphism may give rise to amino terminal extracellular domains and/or other ligand-binding regions that are more or less active in ligand binding, and receptor activation. Accordingly, ligand dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in the anaplastic oligodendroglioma(brain), chronic lyphocytic leukemia, carcinoid lung, large cell lung carcinoma and colon and whole brain. Accordingly, methods for treatment include the use of the GPCR protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or $F(ab')_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the GPCR proteins. Antibodies can be prepared from any region of the peptide as described herein. However, preferred regions will include those involved in function/activity and/or receptor/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that GPCR proteins of the present invention are expressed in the anaplastic oligodendroglioma(brain), chronic lyphocytic leukemia, carcinoid lung, large cell lung carcinoma and colon detected by a virtual northern blot. In addition, PCR-based tissue screening panel indicates expression in whole brain. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in the anaplastic oligodendroglioma(brain), chronic lyphocytic leukemia, carcinoid lung, large cell lung carcinoma and colon and whole brain. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in the anaplastic oligodendroglioma(brain), chronic lyphocytic leukemia, carcinoid lung, large cell lung carcinoma and colon and whole brain. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in the anaplastic oligodendroglioma(brain), chronic lyphocytic leukemia, carcinoid lung, large cell lung carcinoma and colon and whole brain. Thus, where a specific protein has been correlated with expression in a specific tissue, antibodies that are specific for this protein can be used to identify a tissue type.

The antibodies are also useful for inhibiting protein function, for example, blocking the binding of the GPCR peptide to a binding partner such as a ligand. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nucleic acid arrays and similar methods have been developed for antibody arrays.

Nucleic Acid Molecules

The present invention further provides isolated nucleic acid molecules that encode a GPCR peptide or protein of the present invention (cDNA, transcript and genomic sequence). Such nucleic acid molecules will consist of, consist essentially of, or comprise a nucleotide sequence that encodes one of the GPCR peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, human genomic sequences (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the GPCR peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (antisense strand).

The invention further provides nucleic acid molecules that encode fragments of the peptides of the present invention as well as nucleic acid molecules that encode obvious variants of the GPCR proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could␣␣␣␣␣␣at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. As indicated by the data presented in FIG. 3, the map position was determined to be on chromosome 22 by ePCR.

FIG. 3 provides information on SNPs that have been found in the gene encoding the GPCR protein of the present invention. SNPs were identified at 21 different nucleotide positions in exon, introns and regions 5' and 3' of the ORF. Such SNPs in introns and outside the ORF may affect control/regulatory elements.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6× sodium chloride/sodium citrate (SSC) at about 45C, followed by one or more washes in 0.2×SSC, 0.1% SDS at 50–65C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, SNPs, were identified at 21 different nucleotide positions.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. As indicated by the data presented in FIG. 3, the map position was determined to be on chromosome 22 by ePCR.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that GPCR proteins of the present invention are expressed in the anaplastic oligodendroglioma(brain), chronic lyphocytic leukemia, carcinoid lung, large cell lung carcinoma and colon detected by a virtual northern blot. In addition, PCR-based tissue screening panel indicates expression in whole brain. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in GPCR protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a GPCR protein, such as by measuring a level of a receptor-encoding nucleic acid in a sample of cells from a subject e.g., mRNA or genomic DNA, or determining if a receptor gene has been mutated. Experimental data as provided in FIG. 1 indicates that GPCR proteins of the present invention are expressed in the anaplastic oligodendroglioma(brain), chronic lyphocytic leukemia, carcinoid lung, large cell lung carcinoma and colon detected by a virtual northern blot. In addition, PCR-based tissue screening panel indicates expression in whole brain.

Nucleic acid expression assays are useful for drug screening to identify compounds that modulate GPCR nucleic acid expression.

The invention thus provides a method for identifying a compound that can be used to treat a disorder associated with nucleic acid expression of the GPCR gene, particularly biological and pathological processes that are mediated by the GPCR in cells and tissues that express it. Experimental data as provided in FIG. 1 indicates expression in the anaplastic oligodendroglioma(brain), chronic lyphocytic leukemia, carcinoid lung, large cell lung carcinoma and colon and whole brain. The method typically includes assaying the ability of the compound to modulate the expression of the GPCR nucleic acid and thus identifying a compound that can be used to treat a disorder characterized by undesired GPCR nucleic acid expression. The assays can be performed in cell-based and cell-free systems. Cell-based assays include cells naturally expressing the GPCR nucleic acid or recombinant cells genetically engineered to express specific nucleic acid sequences.

The assay for GPCR nucleic acid expression can involve direct assay of nucleic acid levels, such as mRNA levels, or on collateral compounds involved in the signal pathway. Further, the expression of genes that are up- or down-regulated in response to the GPCR protein signal pathway can also be assayed. In this embodiment the regulatory regions of these genes can be operably linked to a reporter gene such as luciferase.

Thus, modulators of GPCR gene expression can be identified in a method wherein a cell is contacted with a candidate compound and the expression of mRNA determined. The level of expression of GPCR mRNA in the presence of the candidate compound is compared to the level of expression of GPCR mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate GPCR nucleic acid expression, particularly to modulate activities within a cell or tissue that expresses the proteins. Experimental data as provided in FIG. 1 indicates that GPCR proteins of the present invention are expressed in the anaplastic oligodendroglioma(brain), chronic lyphocytic leukemia, carcinoid lung, large cell lung carcinoma and colon detected by a virtual northern blot. In addition, PCR-based tissue screening panel indicates expression in whole brain. Modulation includes both up-regulation (i.e. activation or agonization) or down-regulation (suppression or antagonization) or nucleic acid expression.

Alternatively, a modulator for GPCR nucleic acid expression can be a small molecule or drug identified using the screening assays described herein as long as the drug or small molecule inhibits the GPCR nucleic acid expression in the cells and tissues that express the protein. Experimental data as provided in FIG. 1 indicates expression in the anaplastic oligodendroglioma(brain), chronic lyphocytic leukemia, carcinoid lung, large cell lung carcinoma and colon and whole brain.

The nucleic acid molecules are also useful for monitoring the effectiveness of modulating compounds on the expression or activity of the GPCR gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in GPCR nucleic acid, and particularly in qualitative changes that lead to pathology. The nucleic acid molecules can be used to detect mutations in GPCR genes and gene expression products such as mRNA. The nucleic acid molecules can be used as hybridization probes to detect naturally-occurring genetic mutations in the GPCR gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the GPCR gene associated with a dysfunction provides a diagnostic tool for an active disease or susceptibility to disease when the disease results from overexpression, underexpression, or altered expression of a GPCR protein.

Individuals carrying mutations in the GPCR gene can be detected at the nucleic acid level by a variety of techniques. FIG. 3 provides information on SNPs that have been found in the gene encoding the GPCR protein of the present invention. SNPs were identified at 21 different nucleotide positions in exon, introns and regions 5' and 3' of the ORF. Such SNPs in introns and outside the ORF may affect control/regulatory elements. As indicated by the data presented in FIG. 3, the map position was determined to be on chromosome 22 by ePCR. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., Science 241:1077–1080 (1988); and Nakazawa et al., PNAS 91:360–364 (1994)), the latter of which can be particularly useful for detecting point mutations in the gene (see Abravaya et al., Nucleic Acids Res. 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a GPCR gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant GPCR gene and a wild-type gene can be determined by direct DNA sequencing. A variety of automated sequencing procedures can be utilized when performing the diagnostic assays (Naeve, C. W., (1995) Biotechniques 19:448), including sequencing by mass spectrometry (see, e.g., PCT International Publication No. WO 94/16101; Cohen et al., Adv. Chromatogr. 36:127–162 (1996); and Griffin et al., Appl. Biochem. Biotechnol. 38:147–159 (1993)).

Other methods for detecting mutations in the gene include methods in which protection from cleavage agents is used to detect mismatched bases in RNA/RNA or RNA/DNA duplexes (Myers et al., Science 230:1242 (1985)); Cotton et al., PNAS 85:4397 (1988); Saleeba et al., Meth. Enzymol. 217:286–295 (1992)), electrophoretic mobility of mutant and wild type nucleic acid is compared (Orita et al., PNAS 86:2766 (1989); Cotton et al., Mutat. Res. 285:125–144 (1993); and Hayashi et al., Genet. Anal. Tech. Appl. 9:73–79 (1992)), and movement of mutant or wild-type fragments in polyacrylamide gels containing a gradient of denaturant is assayed using denaturing gradient gel electrophoresis (Myers et al., Nature 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the GPCR gene in an individual in order to select an appropriate compound or dosage regimen for treatment. As illustrated in FIG. 3, SNPs, were identified at 21 different nucleotide positions.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control GPCR gene expression in cells, tissues, and organisms. A DNA antisense nucleic acid molecule is designed to be complementary to a region of the gene involved in transcription, preventing transcription and hence production of GPCR protein. An antisense RNA or DNA nucleic acid molecule would hybridize to the mRNA and thus block translation of mRNA into GPCR protein.

Alternatively, a class of antisense molecules can be used to inactivate mRNA in order to decrease expression of GPCR nucleic acid. Accordingly, these molecules can treat a disorder characterized by abnormal or undesired GPCR nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the GPCR protein, such as ligand binding.

The nucleic acid molecules also provide vectors for gene therapy in patients containing cells that are aberrant in GPCR gene expression. Thus, recombinant cells, which include the patient's cells that have been engineered ex vivo and returned to the patient, are introduced into an individual where the cells produce the desired GPCR protein to treat the individual.

The invention also encompasses kits for detecting the presence of a GPCR nucleic acid in a biological sample. Experimental data as provided in FIG. 1 indicates that GPCR proteins of the present invention are expressed in the anaplastic oligodendroglioma(brain), chronic lyphocytic leukemia, carcinoid lung, large cell lung carcinoma and colon detected by a virtual northern blot. In addition, PCR-based tissue screening panel indicates expression in whole brain. For example, the kit can comprise reagents such as a labeled or labelable nucleic acid or agent capable of detecting GPCR nucleic acid in a biological sample; means for determining the amount of GPCR nucleic acid in the sample; and means for comparing the amount of GPCR nucleic acid in the sample with a standard. The compound or agent can be packaged in a suitable container. The kit can further comprise instructions for using the kit to detect GPCR protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et. al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large scale correlation studies on the sequences, expression patterns, mutations, variants, or polymorphisms among samples.

Using such arrays, the present invention provides methods to identify the expression of the GPCR proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the GPCR gene of the present invention. FIG. 3 provides information on SNPs that have been found in the gene encoding the GPCR protein of the present invention. SNPs were identified at 21 different nucleotide positions in exon, introns and regions 5' and 3' of the ORF. Such SNPs in introns and outside the ORF may affect control/regulatory elements.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified GPCR genes of the present invention can be routinely identified using the sequence information disclosed herein can be readily incorporated into one of the established kit formats which are well known in the art, particularly expression arrays.

Vectors/Host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extrachromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in procaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual.* 2nd. ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxyiruses, pseudorabies viruses, and retroviruses. Vectors may also be derived from combinations of these sources such as those derived from plasmid and bacteriophage genetic elements, eg. cosmids and phagemids. Appropriate cloning and expression vectors for prokaryotic and eukaryotic hosts are described in Sambrook et al., *Molecular Cloning: A Laboratory Manual.* 2nd. ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli, Streptomyces*, and *Salmonella typhimurium*. Eukaryotic cells include, but are not limited to, yeast, insect cells such as *Drosophila*, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterokinase. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in a host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kurjan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., *Mol. Cell Biol.* 3:2156–2165(1983)) and the pVL series (Lucklow et al., *Virology* 170:31–39(1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this anti sense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as GPCRs, appropriate secretion signals are incorporated into the vector. The signal sequence can be endogenous to the peptides or heterologous to these peptides.

Where the peptide is not secreted into the medium, which is typically the case with GPCRs, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a GPCR protein or peptide that can be further purified to produce desired amounts of GPCR protein or fragments. Thus, host cells containing expression vectors are useful for peptide production.

Host cells are also useful for conducting cell-based assays involving the GPCR protein or GPCR protein fragments, such as those described above as well as other formats known in the art. Thus, a recombinant host cell expressing a native GPCR protein is useful for assaying compounds that stimulate or inhibit GPCR protein function.

Host cells are also useful for identifying GPCR protein mutants in which these functions are affected. If the mutants naturally occur and give rise to a pathology, host cells containing the mutations are useful to assay compounds that have a desired effect on the mutant GPCR protein (for example, stimulating or inhibiting function) which may not be indicated by their effect on the native GPCR protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a GPCR protein and identifying and evaluating modulators of GPCR protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the GPCR protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence(s) can be operably linked to the transgene to direct expression of the GPCR protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect ligand binding, GPCR protein activation, and signal transduction, may not be evident from in vitro cell-free or cell-based assays. Accordingly, it is useful to provide non-human transgenic animals to assay in vivo GPCR protein function, including ligand interaction, the effect of specific mutant GPCR proteins on GPCR protein function and ligand interaction, and the effect of chimeric GPCR proteins. It is also possible to assess the effect of null mutations, that is mutations that substantially or completely eliminate one or more GPCR protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

What is claimed is:

1. An isolated nucleic acid molecule, wherein the nucleotide sequence of said nucleic acid molecule consists of a nucleotide sequence selected from the group consisting of:
   (a) a nucleotide sequence that encodes a polypeptide having an amino acid sequence comprising the contiguous amino acid sequence of SEQ ID NO:2;
   (b) a nucleotide sequence consisting of SEQ ID NO:1;
   (c) a nucleotide sequence consisting of SEQ ID NO:3; and
   (d) a nucleotide sequence tat is completely complementary to a nucleotide sequence of (a)–(c).

2. A vector comprising the nucleic acid molecule of claim 1.

3. The vector of claim 2, wherein said vector is selected from the group consisting of a plasmid, a virus, and a bacteriophage.

4. The vector of claim 2, wherein said isolated nucleic acid molecule is inserted into said vector in proper orientation and correct reading frame such that a polypeptide comprising SEQ ID NO:2 is expressed by a cell transformed with said vector.

5. The vector of claim 4, wherein said isolated nucleic acid molecule is operatively linked to a promoter sequence.

6. An isolated host cell containing the vector of claim 2.

7. A process for producing a polypeptide having an amino acid sequence comprising the contiguous amino acid sequence of SEQ ID NO:2, the process comprising culturing the host cell of claim 6 under conditions sufficient for the production of said polypeptide, and recovering said polypeptide.

8. An isolated polynucleotide, wherein the nucleotide sequence of said polynucleotide consists of SEQ ID NO:1 or the complement thereof.

9. An isolated polynucleotide, wherein the nucleotide sequence of said polynucleotide consists of SEQ ID NO:3 or the complement thereof.

* * * * *

SEQUENCE LISTING

```
<160> NUMBER OF SEQ ID NOS: 4

<210> SEQ ID NO 1
<211> LENGTH: 2693
<212> TYPE: DNA
<213> ORGANISM: Human

<400> SEQUENCE: 1
ttgctgactc atgtgcccgc agctagcagg agctggcagc atgggctccc cagggctac       60 gacaggctgg gggcttctgg attataagac ggagaagtgg gctctcctcg ccaaaaaagg     120
ctaccaggag cgggacctgg aacccagtt ttccatcatc accaaactca aagggtttc      180 cgtcactcag atcaaggagc ttggaaaccg gctgtgggat gtggccgact tcgtgaagcc     240
acctcaggga gagaacgtgt tcttcttggt gaccaacttc cttgtgacgc cagcccaagt     300
tcagggcaga tgcccagagc acccgtccgt cccactggct aactgctggg tcgacgagga     360
ctgccccgaa ggggagggag gcacacacag ccacggtgta aaaacaggcc agtgtgtggt     420
gttcaatggg acccacagga cctgtgagat ctggagttgg tgcccagtgg agagtggcgt     480
tgtgccctcg aggcccctgc tggcccaggc ccagaacttc acactgttca tcaaaaacac     540
agtcaccttc agcaagttca acttctctaa gtccaatgcc ttggagacct gggaccccac     600
ctattttaag cactgccgct atgaaccaca attcagcccc tactgtcccg tgttccgcat     660
tggggacctc gtggccaagg ctggagggac cttcgaggac ctggcgttgc tgggtggctc     720
tgtaggcatc agagttcact gggattgtga cctggacacc ggggactctg gctgctggcc     780
tcactactcc ttccagctgc aggagaagag ctacaacttc aggacagcca ctcactggtg     840
ggagcaaccg ggtgtggagg cccgcaccct gctcaagctc tatggaatcc gcttcgacat     900
cctcgtcacc gggcaggcag ggaagttcgg gctcatcccc acggccgtca cactgggcac     960
cggggcagct tggctgggcg tggtcacctt tttctgtgac ctgctactgc tgtatgtgga    1020
tagagaagcc catttctact ggaggacaaa gtatgaggag gccaaggccc cgaaagcaac    1080
```

```
cgccaactct gtgtggaggg agctggccct tgcatcccaa gcccgactgg ccgagtgcct  1140
cagacggagc tcagcacctg cacccacggc cactgctgct gggagtcaga cacagacacc  1200
aggatggccc tgtccaagtt ctgacaccca cttgccaacc cattccggga gcctgtagcc  1260
gttccctgct ggttgagagt tgggggctgg aagggcggg gccctgcctg ggatctcaa    1320
ggatgaggcc ccagcatgga ggattggggg tagaattcca cccttgaacc ccagcagaca  1380
gtccctcccc tgactcccac cttggtaggg tgctgcctca gggagccata gaagtcggct  1440
gtgttttgag acggcgacag aacctgaccc gtggagactg ggagagccca gcaggcacct  1500
gtattgcagg gctccgactg catgtggcag gggctcctgc tgcgtctggg cctggaggtc  1560
tctctcccag tgctctgtcc ccagtgttcc tagcagaggt atgcttacca gctgtcagca  1620
cagaccctcc tgctgcctgg gtcctggccc tcctccccca tctgcacccc catcataggt  1680
agagacccca ccctcccatc ggtcctacat ggggctgtgc agctggagcc aaaaaggcaa  1740
ggcagaaaga ggagtgatgg gggagggga ttgtttcagc ttctctggtg ctgtgatgcc    1800
ccaggagagt cctaatctag ggaatggggt ggagtaggca gataatccac ctccctatcc  1860
cccaggcaag ggcggagcat gtgtcttggg cccacacctg cttagtttat gaggaccggc  1920
tgctttccag tggtagccct tttgccatgg aggtctggga gagagagcag agggcggcag  1980
ggctaagttg gtgatcattg ggttcttcag gaccttctat atccctcctc ggtaacccc    2040
cagcccaacc ccttggaatc tttcctccag gcttcctgag agccctgggg gtgggaggct  2100
gtgggaggct gtacatctga aattcacttc agtccaagtc ataccctagga agctgtctgg  2160
gcagctgctc gagggaggcc ctggctctga tcccaggctg gatggagtgg ctggaaggaa  2220
tggttccaaa caacaccacc gagatctccc tcaggctggc caggttttgc agctggaatt  2280
ctcctcttgg tcccagggcg gggcagggaa ttctaagtgt ccaccccagg gaggcaaggg  2340
gctgctttcc actgtgggta cctggtgatc agggcaagct gtggagggcc aggggtgggg  2400
ctgagactgg gctgacatct agaatcacct gccacctgga gcctcagtaa aatgcctggg  2460
gtccctgctg cctctcaatc tccagagcca tgtccatggg gaggtgggct ctgaagggcg  2520
aaggtgggag agcagggccc ctgaggcctg ggtatccaag gaggggcacg tgcacctgat  2580
tctccttggg gcccagagga agctgatgtc atggctggac aaagtcacgg agtaaagcca  2640
gcaaagccac caaaaaaaaa aaaaaaaaaa aaaaaaaaaa aaaaaaaaaa aaa          2693
```

<210> SEQ ID NO 2
<211> LENGTH: 405
<212> TYPE: PRT
<213> ORGANISM: Human

<400> SEQUENCE: 2

Met Gly Ser Pro Gly Ala Thr Thr Gly Trp Gly Leu Leu Asp Tyr Lys
 1               5                  10                  15

Thr Glu Lys Trp Ala Leu Leu Ala Lys Lys Gly Tyr Gln Glu Arg Asp
                20                  25                  30

Leu Glu Pro Gln Phe Ser Ile Ile Thr Lys Leu Lys Gly Val Ser Val
            35                  40                  45

Thr Gln Ile Lys Glu Leu Gly Asn Arg Leu Trp Asp Val Ala Asp Phe
        50                  55                  60

Val Lys Pro Pro Gln Gly Glu Asn Val Phe Phe Leu Val Thr Asn Phe
65                  70                  75                  80

Leu Val Thr Pro Ala Gln Val Gln Gly Arg Cys Pro Glu His Pro Ser
                85                  90                  95

Val Pro Leu Ala Asn Cys Trp Val Asp Glu Asp Cys Pro Glu Gly Glu
            100                 105                 110

Gly Gly Thr His Ser His Gly Val Lys Thr Gly Gln Cys Val Val Phe
            115                 120                 125

Asn Gly Thr His Arg Thr Cys Glu Ile Trp Ser Trp Cys Pro Val Glu
            130                 135                 140

Ser Gly Val Val Pro Ser Arg Pro Leu Leu Ala Gln Ala Gln Asn Phe
145                 150                 155                 160

Thr Leu Phe Ile Lys Asn Thr Val Thr Phe Ser Lys Phe Asn Phe Ser
                165                 170                 175

Lys Ser Asn Ala Leu Glu Thr Trp Asp Pro Thr Tyr Phe Lys His Cys
            180                 185                 190

Arg Tyr Glu Pro Gln Phe Ser Pro Tyr Cys Pro Val Phe Arg Ile Gly
            195                 200                 205

Asp Leu Val Ala Lys Ala Gly Gly Thr Phe Glu Asp Leu Ala Leu Leu
            210                 215                 220

Gly Gly Ser Val Gly Ile Arg Val His Trp Asp Cys Asp Leu Asp Thr
225                 230                 235                 240

Gly Asp Ser Gly Cys Trp Pro His Tyr Ser Phe Gln Leu Gln Glu Lys
                245                 250                 255

Ser Tyr Asn Phe Arg Thr Ala Thr His Trp Trp Glu Gln Pro Gly Val
            260                 265                 270

Glu Ala Arg Thr Leu Leu Lys Leu Tyr Gly Ile Arg Phe Asp Ile Leu
            275                 280                 285

Val Thr Gly Gln Ala Gly Lys Phe Gly Leu Ile Pro Thr Ala Val Thr
            290                 295                 300

Leu Gly Thr Gly Ala Ala Trp Leu Gly Val Val Thr Phe Phe Cys Asp
305                 310                 315                 320

Leu Leu Leu Leu Tyr Val Asp Arg Glu Ala His Phe Tyr Trp Arg Thr
                325                 330                 335

Lys Tyr Glu Glu Ala Lys Ala Pro Lys Ala Thr Ala Asn Ser Val Trp
            340                 345                 350

Arg Glu Leu Ala Leu Ala Ser Gln Ala Arg Leu Ala Glu Cys Leu Arg
            355                 360                 365

Arg Ser Ser Ala Pro Ala Pro Thr Ala Thr Ala Ala Gly Ser Gln Thr
            370                 375                 380

Gln Thr Pro Gly Trp Pro Cys Pro Ser Ser Asp Thr His Leu Pro Thr
385                 390                 395                 400

His Ser Gly Ser Leu
            405

<210> SEQ ID NO 3
<211> LENGTH: 16449
<212> TYPE: DNA
<213> ORGANISM: Human

<400> SEQUENCE: 3
tctccaagtc catgggtgcc tggtaggaga caggggatg aatgtgaacc cctgcatggc    60
tatagccacc tgcctcctcc cctgccctgc atcactacct ggcctatttt ttgcctctag   120
aagcactgct tcctatgctc cttaggacca ctgcccgcat atgacagata gaacatcga    180 ggctaaggca acgcaaatct tttccttaaa gtcatacagc tgtcaaaaga agctggaca    240 acctgggcaa catagcgaga taaaaaatta tttaaattag ccagatgtgg tagcccctg    300

-continued

```
tagtctcagc gactcaggag gctgaggcag gaggctcacc agagtgcaga gttcaaggat    360
gcagtgagct atgatcctgc cactgcactg aaagctgggt gacagagcaa gaccctggct    420
ctaataaatg aatacataaa gtctcacagc tagtggtagc taatcctgcc agagtcaggc    480
ctctacctgt ctgatgacaa atggcacact atgtctttta acctgattgc agaccacaaa    540
tgttttgtga atattttccc cagggaaaaa accggaagta gttctaaatt ctatacatcc    600
attatattag ttttacctgt ggattgggaa aacccagctc tgattgcatt tcagggcggg    660
acagcctttg gtgcactgtc tggcgggatt ttccatttta acctccttct agaagcgcct    720
tctcatggta aagttcctga tgccgccagg agcgccgagg agagggcagg gggctggaga    780
cgccccgcag agggctacgt gccctgctgg acagaggtct cctgcctcct cggcggcgcc    840
agcccacctc ccacaacccc tgcgggagaa gcccccaagg ggaggagacg ggcctggccc    900
ctgccccgag caccttccgt ctctaggtcg gagtctgaat cggccttggg accctgcttg    960
gcttcgggga cccctgcaag acgtccacag gccgccgtcg cctcttcctc ctgctttta   1020
tcctccccag acctctggca ggaaccgctc atcgttacgc cctttcgca gcctcagacc   1080
ctgaggcgga gaccgcttgg cgcctcactt agagcgcgac ccggggatgt gggcggagtc   1140
tgcggctgcg ctgaccaatc gagtgtggcg tccatcgact ggcgtctgcc acggcaatta   1200
gcgacgcgct ccccgcggc ggtcgccccg gcaacccagt gctgtaggtt gccgtagaaa   1260
ccgtggctct cctgcgctga ggctcctcgc ctgagaggat aaactgcacg cgccacgggc   1320
tatgcactgg gctgggcgcc ttgtgggcat cctccctgcc ttcctagggg gttccagcat   1380
cgccccctt tcgtggactg ggaaacacgc ctgactccag gacttgtgtt gtcctcactg   1440
cactggggaa ggtggcgggg gcagcttttc aggagggcct ggggaacttc gcagagccag   1500
gtcaccctct cactctgtgc ctcttagtta tcttgcatgc tctggtcttt gcatacgctg   1560
ctccctgcac caggaacctc catccccatc tttgtctgct tgtcgaactt cagaaatctg   1620
caagggtcag cttagaggtc acttcttccg gaagctttcc tcaacaccct ccccgccctg   1680
ctgctgctgc cctcaggccc tcctctcaca gcactgataa cagctgtccg tctccaccct   1740
cccaccacct ccactcccac cccaggaagt gaggccagag ggcagggaca gagctgctgc   1800
tgttctctgt gtgccagggc ccagcaaagg gaatgtaggg aggtgggag gtgcagggca   1860
gctgggatta ggggttgagg gctgggtgtt ggaggctgga tctggatcct gctttagtgg   1920
aagtgtccct ttaacagcaa ctggcctggc ctggctcggg ccctgctttg cctcctgttc   1980
agctgcggct gcagctgcca tgctgactca tgtcccgca gctagcagga gctggcagca   2040
tgggctcccc aggggctacg acaggctggg ggcttctgga ttataagacg gagaagtatg   2100
tgatgaccag gaactggcgg gtgggcgccc tgcagaggct gctgcagttt gggatcgtgg   2160
tctatgtggt agggtaagag agaagagctt ttggccaggc tggagggca agggaagagg   2220
tgggggtgg ggcttggtcc tgctgggttg aagttgaggg ttgggctgtt tagggctgg   2280
agtggaaggg ggcagattgg gacggggttg gggagagcta ggcgatacaa gacaggagag   2340
caagaacaag ctgtgtgttt gtcctgtgtg tccacttgcc tccttcccag gcccccaccc   2400
aggccccacc cagggggcac atgacatagt ccttaacatc tgtgagagct ggagcactag   2460
gcccccagag agaccaccag ctgtatctcg ggtcaggaga gtctgtaagg gggaagctgg   2520
atctagtcag gctgggggtg ggtgctggct agtgaaggtg attgtctgag ggcattggct   2580
ctctgatgca tggctggagc ttctgtctca ttcagggggt ctggagtggg aagtggggcc   2640
agagaggagg tggggccttc gatgttgggc cgggagcctg tagggtgtgg ggggagaact   2700
```

-continued

| | |
|---|---|
| gagcatgtag ggctcagctc cgccctgtc actacacgct ggggacacac cacactgccc | 2760 |
| gacttctcct ccccaggtgg gctctcctcg ccaaaaaagg ctaccaggag cgggacctgg | 2820 |
| aaccccagtt ttccatcatc accaaactca aggggtttc cgtcactcag atcaaggagc | 2880 |
| ttggaaaccg gctgtgggat gtggccgact tcgtgaagcc acctcaggtg ggggccctga | 2940 |
| tgttgctgac gggggcgcaa gtcctttccc cactgcacag ctgaacaccc gccatgcagc | 3000 |
| cagtgtgtgc gagagagaag catgtgatgc cagagacggc tgcggttct caggaagggc | 3060 |
| ttcacagagg agtggcacct ggacaggact ttcaggatg tgtaggaggt tttgggtgg | 3120 |
| aaaaagggc cactcaagaa gccaggccag ggttggacgt gctggctcac gcctgtaatc | 3180 |
| ccagcacttt gggaggccga ggcaggtgga tcacgagatt gagagtatcc tggctaacac | 3240 |
| ggtgaaaccc catctctatt aaaaatacaa aaaattagcc gggcatggtg gtgggcgcct | 3300 |
| gtagtcccag ctactcggga ggctgggca ggagaatggc atgaaccgg gaggtggagc | 3360 |
| ttgcagtgag ccgagattgc accactgcac tccagcctgg gtggcaaagc gagactctgt | 3420 |
| ctcaaaaaaa aaaaaaaaaa gccaggccag agaaactgca tttccaaaga ctgccaacag | 3480 |
| aaaagaaggg agtgtccagg actaatggct tgagcttgag agtggtgtga ggtgctgggg | 3540 |
| catgaacctt ccctgtagcc ctgctccctg acctggggca ctacggtcag gtgctgctcc | 3600 |
| tccctcttc tcggctgcgt tttcctcctc cctccaccca gctcatcccc agcctcaact | 3660 |
| gccacttctg ctcctctgat gcccagggtg tattcccagt gatcacctgc ccagagcaca | 3720 |
| gctgtcttct aggtgcacac ccacatgtcc aaagatcaat tatttcctc tcctggcatg | 3780 |
| gcctctgtga cgcccactag tcatggtggc tgtgacatcc actagtgcct cagccagacc | 3840 |
| cgtgactcac cctggacccc ttcctgtccc ttccaagatt tttcaccact acccatgcca | 3900 |
| tgccatgcat gagactatgg cctcctagag ggtccctaga tgcccctctc gcctcctccc | 3960 |
| ttactgctcg gtgcacacca cgcagcagcc aagctgaact ttcacaccag gcatcatgag | 4020 |
| agcctgcagc gcctgcttct accctcagga attcccccaa ccctgcccat gacggtgtcc | 4080 |
| acactttcct cccaatccta atggctgcca ctcccagcac catctggcca gccctcacct | 4140 |
| tcccttcctg ggcatacatt ccccaaattc acagtgctct cacgagcagc actggagggt | 4200 |
| cagccttct ttccaatgtc ctcggccacc cgttgaccac agacacagct ttccctcttc | 4260 |
| tcccttggcc cctgccatgc cagtgctgct gtgtgtgaga tgggagactc acctcgtctc | 4320 |
| catcctgagc aggtgctggg cccagctctc ccttggatct tcagtactag aagcagcagg | 4380 |
| ctgttggaat attctggttg gagccaggca tggtagctgg agcctgtagt cccagctact | 4440 |
| tgggaggctg aggcaggagg acctcttgag tccaggagtt agaggttgca gtgagcactg | 4500 |
| atcacaacac tacactccag cctgggtgac gaagtgtaat cctgtctcta aatacacaca | 4560 |
| tacacatgca cacacacaca caaattttgg ttgagacaag agacttgtct caagagatgg | 4620 |
| acatgggcac aaggcttcct ggtctcaaaa atggccagaa ccactgccag cctcccatct | 4680 |
| ctgcttcagt ctgccttaca gggggacagg gttaatgact tgatgggcc aacatcccctt | 4740 |
| ccctcataaa ccaggctgcc ggcttccggc ctttccagtc aacacgagcc cagccaggcc | 4800 |
| aaccttgaga cttgcctcct agggagagaa cgtgttcttc ttggtgacca acttccttgt | 4860 |
| gacgccagcc caagttcagg gcagatgccc agaggtgagt ttacccagga tcctcccagc | 4920 |
| gggtcccttg ttcctccatc agccccaggt ggccacccgt gtttcccttt ccccttccca | 4980 |
| ggtggctgaa ggctcagcct gtgctcggtg tcccccaggc actgggctac atctttcct | 5040 |

```
gaatcattat gttcagtctt cacatatccc ctgcctggta ggaagtcctg tgatccccat    5100
ttcagaggag aagactgagg ctcagtgagg ttgagtcact ttcttaaggc ctccaggcct    5160
gtgggtgaca ggaccccgag ctctgggcag cagcagttcc catgaggtgt ccaggccctc    5220
ccatcctggt cctgcctctg ggtactctcc aggttggtag tgtgacaccc agagctgcgc    5280
acatgctcag ggaggttcta atagcaagag ccaagctgga atatcacctc cccttgtctg    5340
tgcccagcct ctattaatat gtcctgaggc agctttcatc tttgtgggcc aacacagcac    5400
actcttgctc atggtgaatt caggattgct tatgatttct ggatagtttt ttttgttttg    5460
tttttgagac ggagtttcac tctgtcaccc acgctgagt gcagtggcag atatcagctc     5520
actgcaagct ctgcctctca ggttcacgcc attctcctgc ctcagcctcc ggagtagctg    5580
gtactacagg cgcctgccac cacgcccagc taatttttttt tttttttgt attttagtg     5640 gagacggggt ttcacggtgt tagccaggat ggtctccatc tcctgacctc atgatccacc    5700
tgcctcggcc tccaaagtg ctgggattac aggcgtgagc caccgcccc ggcctgattt       5760 ctggatagtt tttacatcaa ccgtggtcaa gccagagtcc cccaccttgt tcttcttcat    5820
ttctgatcca gaaatgctga ttctcccct gacatttcac cttttcccct tgcctgggga     5880
tgtccctggg atcctgcatc tgtcacagag catgctcatt ctctccagct gtgaattttg    5940
tttgaactat tgggactcag gacatagtcc tgaaagttta cctccacagt gacatcttta    6000
ggcaagtcca acatttacgt gcctcctggg ctggagggtc gttgtgcaga cagctgtccc    6060
ctgagccctg gtggctggtc ctagcacagt tgctggagac atcccatgtc cgtagttgga   6120
aatatgcaca aaggattgct tactcttttt gtttgtttgt ttttttgaga tggagtcttg    6180
ctcttgtccc caaggctgga gttcaatggc acgatctcgg ctcactgcaa cctccgcctc    6240
ctgggttcaa gcagttctcc tgctcacccc ctgagtagct gggattacag gtgcccgcca    6300
ctgtgcccag ctaatttttg tattttaagt agagacgggg tttcaccatg ttggccaggc    6360
tggtctcgaa ctcctggcct caggtgaccc accagcctcg gcctctcaaa gtgctgggat    6420
tacaggcgtg agcctgccga gagcttggtc ggggagacct gaacccagcg gtgctaaagg    6480
aattaaagac aaacacacat aaatatagag gtgtggagtg ggaaatcagg ggtatcacag    6540
ccttcagagc tgacagcctc gaacagattt acccacatat ttattgacag caagccagtg    6600
ataagcattg tttctaccag attatagatt aactaaaagt attccttatg ggaaacaaag    6660
ggatgggctc tggttggtta tctgcagcag gagcatgtcc ttaaatcaca gatcgctcat    6720
gctattgttt gtggtttaag aacgccttta agcggttttc cgccctgggt gggccaggtt    6780
ttccttgccc tcattccggt aaacccacaa acttccagtg tgggtgtcgt ggctatcaca    6840
aacatgtcac agtgctgcag agattttgtt tatggcagat ttttgggggc ctcttcccaa    6900
catgagccac tgtgcctggc aggatgtgct tactcttggt gaaccacac aatgtccttc     6960 tctttcttaa tgctcagatg tgcatttagt gttcagtttg tagaccgttc tgaaatttgg    7020
ctggatctgt gggtctgtgt ttttcagaat ctgtgcaatt cctctttgtc tgcaaccaca    7080
cttctggctc ttcccatgaa acgtcagggc tgggtcgtaa ttatcagatc tgacaacctg    7140
gctttcccgg aagaccagag ttctgccagc tcctctaggg atcctggtgc ctgatccctc    7200
ccttacatgc accatgctct ttatagtgtc acctccctca gcagacaccg ctgagcctcc    7260
ccgctgggcc aggggctag ctaggctaaa ttcacaaaac tccatctccc atacttcaaa     7320
gaccacccac atgacagcc cagcccaggt ggcaggtccg atgatgggac agaggctgta     7380
ggtgggggac ctagggctgc acttgagcag aatcttttttt tttttttct tttttttttt   7440
```

-continued

```
tttgagacag agtctcgctc tgtcacccag gctggagtgc agtggcgtga tctcggctca    7500
ctgcacacct ccacctcctt ggttcaagcg attctcctgc ctcagcctcc caagtaggtg    7560
ggactacagg cacacaccac cacactcggc taattttttgt attttttaata gagacagggt  7620
tttgctgtgt cggccaggct ggtctcgaac tcctgacctc aggtaatccg cccaccttgg    7680
cttctcaaag tgttgggatt acaggtgtgc caggccaagc agaatcttaa aaaaggtgg     7740
ggagaagctg gtgagcaggt ggatttggtt gaagcaggat gtcgacacag agggggcttg    7800
gtgggtaaag gccctgagct gtgtgaggtg aggtgccttt agggctacct gccactgggt    7860
ggagctgaag tgaagatttg gactggggtg ggaagaaggt agttcaggat ttcaggggcc    7920
cctgtaagcc ccactaagga gctaaactgt ttttgtttgt ttgttttctt tttctctttt    7980
cttttttttc ctgtagcaat gaggtcttgc tttgttgccc aggctggtct cgaactcctg    8040
agctcaggca atccgcctac tttggactct caaagtgcta ggattacagg cgtgagccac    8100
tgtgcctggc aggagctaaa cttgattaga ggaacagaag agagccacac gtgggctcag    8160
aggcagggtg ctcagtttcc tgcacattgg gatgcaccac ttgggctgct gggcataggt    8220
ggatgagggt atgggaagac gtgggggccc cactggtggt cactgtgggg tctagttgga    8280
ggagacggta gcccagctgg ggtgaagagg agaggcagac acaggacata ggtagggaca    8340
aagaagcaga gcatgtggct ctgctccgac ctccacccaa tcacgacggc cctgtctttc    8400
agaaagtccc accgcctcat tctggcttct cagaggccct cagccttcct tgcgcccctg    8460
gtgctggtgt tcttcctgct gccccctgagc tgagtgccct gggcagcagt gtccatcctc   8520
agttggggca ggaccatgcc tgggagagtg cccgatgctc aagggtgcct tcgtctctgg    8580
ggtctgggac cccagaaagc tcacctgtcc tccccttctg ccagagcccc atagtcccat    8640
gcctctgtgc aggcattaat gtccccaggt tacagaagag cgagcaggaa ggagtagcct    8700
gtggtccctc agcaagggtg tggggtcctg cttcaatacc caagcccctg actctagggc    8760
cctgatcttt gtcagctatg tccccatgcc gggcatcaaa aactcaccct cccaaggtat    8820
cttcaccttc cctgatctgt catccaaatt ggaccagagg agctagacct ggaagaatca    8880
cttccgcatc caccagggac agaactgtca ggagggaagg ggcagggtgc gttgtctcac    8940
gcctgtaatc ccagcactct gggaggctga cacagaagga ttgcttgagg ccaggagtta    9000
aaaaccagcc tggtcaacat agcaagactc catctctaca aaaaaaaaat attaaaaaat    9060
cagccaggca cagtggtgtg tgtctgtagt cccagctact gggaatactg aggtgagagg    9120
attgcttaag cccgggaggg cgaggctgta gtgagccatg atcataccac tgcactagag    9180
cctggacaac agagtgagac cgaatcacta aaaataaatt ttttgaaaaa ggaggaaagg    9240
ggtctccctt tgtctttgaa atacagtact gtaccttcat ctggccaggg cattgctccg    9300
ctccctcctc tgaccacctc cttttatttg cacctccag cttcctgtg tggccccaca     9360
ctcagggtac tctggcggcg gggtggtgag gttgtttaag gtgggaaggg ggcctgtcct    9420
tcccaccttg aacctccctg cctttgagac tgggctgtgg aggggagaca tcccctgtgc    9480
cattggtgac tgctctctct cccacctcag cacccgtccg tcccactggc taactgctgg    9540
gtcgacgagg actgccccga agggaggga ggcacacaca gccacggtaa ctgtgggctc     9600
tgtcttccag tgcccctagc agggtggggg ccggctgggg atcctgggtg gctcctgagt    9660
gcaggccctg ctcgcctctg tccctgcatc tctctttctg ccaacaaccc cctggctgaa    9720
ggcctcccca ggcctgcaga gatttgaagg tctggagttc atctttgtt ttctaggtgt     9780
```

-continued

```
aaaaacaggc cagtgtgtgg tgttcaatgg gacccacagg acctgtgaga tctggagttg   9840
gtgcccgtg gagagtggcg ttgtgccctc gtaagtgtcc ccacaatccc ctaccccaac    9900
tggcgcaggg ccccaggcct ggcagaggct gtcacctccc ttccacctgc aggaggcccc   9960
tgctggccca ggcccagaac ttcacactgt tcatcaaaaa cacagtcacc ttcagcaagt  10020
tcaacttctc taagtaagca gagtgggtct catctgcccc aagaccctcc ttgtccccta  10080
cctcatctga cctttcccac tcctcccagg tccaatgcct ggagacctg ggaccccacc   10140
tattttaagc actgccgcta tgaaccacaa ttcagcccct actgtcccgt gttccgcatt  10200
ggggacctcg tggccaaggc tggagggacc ttcgaggacc tggcgttgct ggtgggtccc  10260
aagttggggg cagggttcct agagggctct gggagagggt cccgggccca cccaccggtg  10320
gaaaagctat gtgctatgtg cagggtggct ctgtaggcat cagagttcac tgggattgtg  10380
acctggacac cggggactct ggctgctggc ctcactactc cttccagctg caggagaaga  10440
gctacaactt caggtgaggc cccactgctc ccagtgccca gctgctgggc ccatcgccct  10500
ctcactgtgg cggccaggac agaccacacc caggcccagg cctctagata ttccactacg  10560
tgtgcaaggg ggtcccagga gcaggagaga gctgttctca accccacatc ctccagcaca  10620
ggctccgtcc tgctgcccca agtcctgagc cctccacccc atctgtccca ggcccctgcc  10680
cagctcaggc tcctcactgc cagcccttcc tccaccccac ctcgcttcta gtatctcccc  10740
tccacagcaa tggggtgttt cattttact ttcccttct ccccttcagc tttgttttttt    10800
tttttttaag acagaatctc attctgtcac ccaggctgga gtgcagtggc ccgacctcgg  10860
ctcactgtaa cctctgcttc ctgggttcaa ccgattctcc ttcctcagcc tcctgagtag  10920
ctggaattac aggtgctcgc cactactccc agctaatttt tatattttgg tagatagaga  10980
tgggttttca caatgttggc caggctggtc tcaaacccct gacctcaggt gatccaccca  11040
cctcagcctc ccgaagggct aggattacag acgtaaacca ccatgtctgg cctcccttcc  11100
gcttttacct aaacttttt ttttttttg agatggagtc tcactctgtc gcccaggctg    11160
gagtacagtg gcgggatctc agctcactgc aagttccgct tccgtgttc acgccattct   11220
cctgcctcag cctcccaagt agctgggact acgggtgcac gcctccacgc ccggctaatt  11280
tttgcatttt tagtagagac agggtttcac catgttggcc aggatggtct cgatctcttg  11340
acctcgtgat ccacctgcct cagcctccca tagtgctggg attacaggcg tgagccacca  11400
cgcccgacct tttttttga aacggagttt tcactttctt gtagtccagg ctggaatgca  11460
atggcgtggt cttggctcac tgcaacctct gcctcctggg ttcaggtgat tttccagcct  11520
ctgcctccag agtagctggg atgacaggt tgcaccacca cacccaacta atttttgtat   11580
ttttagtaga gatggtgttt tgccatgttg gccaggctgg tctcgaactt ctgacctcag  11640
gtgatctgcc cacttcagcc tcccaaagtg ctgggattac aggcatgagc caccaagcct  11700
gttttttttg tgtttttttt tttttttttt ttagatgaag ttttgctctt gttgcccaga  11760
ctggagtgca gtggcccgat ctcggctcac tgcaatcttt gcctctcggg ttcaagcaat  11820
tctcctgcct cagcctcctg agtagctgtg attacaggtg cacaccacca cccagcta    11880
atttttgtgt ttttactaga gatggggttt caccatattg gtcaggctgg tctcgaactc  11940
ctgacctcag gtgatccacc tgcctcagcc tcccaaagtg ctgggattac aggtgtgagc  12000
cactgtgcct ggcctcaagt ttcataaatt gcatttatta tcatgtcttt gagtcttcta  12060
agcagatcta ttgatccctt ctgccaccga gcgtcacctc gtcatgcagg caggcacaca  12120
cgaccaccag gcctggggat gatgcccctc aacatagctc actgcacccc gtctgatctg  12180
```

```
gcttccccaa cctccccagc ccttcgaaac cacgtggggc tggctcccac ccacatcctg   12240
ttcccctgac ctctgtgctg gcaaaccacc tgtgtgcatg ttccttcagg cccagcctca   12300
tgtcccctcc aggaagtcta ccccagttcc cagggaagag tgagttccca tctctggaat   12360
ccctcagccc tgagcctgcc ccttcacatc ccccgctgct gggtctgttt agggactcct   12420
ctgtcccccg tcctctcagc aggcagggaa cttctgaggg acaggtcttc gtttgctttt   12480
tctgttttct caccaattac atagggctga gacccaggac tcaggcttgg gctggggtt    12540 tatagagtca attgacaagt tggacagagg tctggcaggg ccagcccac ctgggggtgg    12600 gcaaagcagg tcaccagagc cttctttcct gcccacagga cagccactca ctggtgggag   12660
caaccgggtg tggaggcccg caccctgctc aagctctatg gaatccgctt cgacatcctc   12720
gtcaccgggc aggtaggcac aggtaggggt caggccgggg atgggatggg gcaggcagac   12780
agggctggag gaggcatgag gctgacagtc gtgggctgag aggttcagct cagatctctc   12840
tcaggcaggg aagttcgggc tcatccccac ggccgtcaca ctgggcaccg gggcagcttg   12900
gctgggcgtg gtgagtgcga gcactgtggg cacctgcagg ctgcagtgag tgctgctgac   12960
cagggtgtgt ccaatgcatg ctggagcctc cggtgcctgc acattgagtc tcggggtgca   13020
ggctggggag gtggcaggag agcaggctcg ggggctggaa catgggttgg ccctgcctct   13080
cccaggtcac ctttttctgt gacctgctac tgctgtatgt ggatagagaa gcccatttct   13140
actggaggac aaagtatgag gaggtgagct gaggtcgctc tgcttggacc ctgggttctg   13200
ccacacttag gaagatgttg gctggatccc tgacctgctg tcctcatctg caggccaagg   13260
ccccgaaagc aaccgccaac tctgtgtgga gggagctggc ccttgcatcc caagcccgac   13320
tggccgagtg cctcagacgg agctcagcac ctgcacccac ggccactgct gctgggagtc   13380
agacacagac accaggatgg ccctgtccaa gttctgacac ccacttgcca acccattccg   13440
ggagcctgta gccgttccct gctggttgag agttggggc tgggaagggc ggggccctgc    13500
ctggggatct caaggatgag gccccagcat ggaggattgg gggtagaatt ccaccttga    13560 accccagcag acagtccctc ccctgactcc caccttggta gggtgctgcc tcagggagcc   13620
atagaagtcg gctgtgtttt gagacggcga cagaacctga cccgtggaga ctgggagagc   13680
ccagcaggca cctgtattgc agggctccga ctgcatgtgg cagggctcc tgctgcgtct    13740 gggcctggag gtctctctcc cagtgctctg tccccagtgt tcctagcaga ggtatgctta   13800
ccagctgtca gcacagaccc tcctgctgcc tgggtcctgg ccctcctccc ccatctgcac   13860
ccccatcata ggtagagacc ccaccctccc atcggtccta catgggctg tgcagctgga    13920 gccaaaaagg caaggtagaa agaggagtga tggggaggg ggattgtttc agcttctctg    13980
gtgctgtgat gccccaggag agtcctaatc tagggaatgg ggtggagtag gcagataatc   14040
cacctcccta tccccaggc aagggcggag catgtgtctt gggcccacac ctgcttagtt    14100
tatgaggacc ggctgctttc cagtggtagc ccttttgcca tggaggtctg ggagagagag   14160
cagagggcgg cagggctaag ttggtgatca ttgggttctt caggaccttc tatatccctc   14220
ctcggtaacc ccccagccca accccttgga atctttcctc caggcttcct gagagccctg   14280 gggtggag gctgtgggag gctgtacatc tgaaattcac ttcagtccaa gtcataccta     14340
ggaagctgtc tgggcagctg ctcgagggag ccctggctc tgatcccagg ctggatggag    14400
tggctggaag gaatggttcc aaacaacacc accgagatct ccctcaggct ggccaggttt   14460
tgcagctgga attctcctct tggtcccagg gcggggcagg gaattctaag tgtccacccc   14520
```

-continued

```
agggaggcaa ggggctgctt tccactgtgg gtacctggtg atcagggcaa gctgtggagg      14580
gccagggtg gggctgagac tgggctgaca tctagaatca cctgccacct ggagcctcag       14640
taaaatgcct ggggtccctg ctgcctctca atctccagag ccatgtccat ggggaggtgg     14700
gctctgaagg gcgaaggtgg gagagcaggg cccctgaggc ctgggtatcc aaggaggggc      14760
acgtgcacct gattctcctt ggggcccaga ggaagctgat gtcatggctg acaaagtca      14820
cggagtaaag ccagcaaagc caccctcttc ctgtgtagtc cttacaggca tgactggaaa    14880
gttgggggc atctatggta gacatggcac agccatgaag agaccagtgg ggtggtgcag      14940
ggtggacttg ggaccctac ccctgaagac tgaggccctg cagctaccag gtgggctaga      15000
aggtaactgg aacaggcctg ggacttgtg cacccatgta ggagcatgag gccacactc      15060
ttttcacctc aaagcccttg aagagtgggc aaagacagca agagagctgc agcctgggcc    15120
cgagctcaga aacagctgtc gcctcagtct gcgcacaggc atgcacccca gggtagtgcc     15180
tgcagggatg catgtgtccc cgtggggtg cctgtgccag gcaggcctca ggtgcatgcc      15240
atgctcagaa ccctgctgcc ctttctaggc agcctccttg gggcccaagc tctgctccct    15300
ggatctgcca cctagcagac gtggggagcc tgaccccatg cctgtcatgg aaccctcctt     15360
gcctggtgtg tgtggctccc ctcttcactg ggcacctgga tccaggccca cctgtgtccc    15420
tgactcaggg tggtcccagg actggcacct actctttaga gagccccagc atctttgatg    15480
tggattggag acaattgcct ggttccctgg ggcaggtgaa gacttggtgc acaaagaat      15540
gccacagtgg atacgccagc aggccacatg gctggccaag caattattat tatggatccc     15600
ttgggctgtg ggccttccca tccacccccac cacaactgcc caggtagctg agctgatca    15660
taaacaagaa ggctctgggc agagtccatg gcaccagcac cagccaaggc ccactcctga    15720
agacccgaag cccagcccct ggatgaaggt cctaaggtcc tgaggactcc ccagcctgtg    15780
caggcctgca aacccaggct gcccacaaca gaagggctc tcggcttgtc tggcctctct     15840
ggcctcccaa gcaggtgtgg gagggcgggg caagtgtggg ctgatcagct actccatatg   15900
gccagggtcc tgtgctggtg cctggctggg gggctgcata gcctgcactg tctcctccag   15960
gctgcccctg gggaatacca cgtagtgtgt ggagttcagc cctggcagct cccgctggtt   16020
ctccttgcta tgccggatgc catagccgaa atacactgca agtcctagac agggcaggag    16080
gcagggcatg agcctgaggt acaggttcca gcccttcctg tcctctttgc cctcctcctg    16140
acccccggtcc cagcctggcc cccactcacc catcagcagc cagatggaga agcgcaccca  16200
ggtcagatag ctaagtttca gcatgaggca gatgttgagg acgatgctca gggctggaat   16260
caggggaacc atggggatct gaggaggcag aggcagggca gggctggggcc gggctgcagg   16320
aaagatctgc cagcccaggg ctcactttct cgggaatcca tagagccttt gttcctcacg    16380
ggagattgtg gagacatgtg ctcactcacc atgcagaaag gggtgcggga tgggtgtgtg    16440
gtcctcccc                                                             16449
```

<210> SEQ ID NO 4
<211> LENGTH: 431
<212> TYPE: PRT
<213> ORGANISM: Human

<400> SEQUENCE: 4

```
Met Gly Ser Pro Gly Ala Thr Thr Gly Trp Gly Leu Leu Asp Tyr Lys
 1               5                  10                  15

Thr Glu Lys Tyr Val Met Thr Arg Asn Trp Arg Val Gly Ala Leu Gln
            20                  25                  30
```

-continued

```
Arg Leu Leu Gln Phe Gly Ile Val Val Tyr Val Gly Trp Ala Leu
         35                  40                  45
Leu Ala Lys Lys Gly Tyr Gln Glu Arg Asp Leu Glu Pro Gln Phe Ser
 50                  55                  60
Ile Ile Thr Lys Leu Lys Gly Val Ser Val Thr Gln Ile Lys Glu Leu
 65                  70                  75                  80
Gly Asn Arg Leu Trp Asp Val Ala Asp Phe Val Lys Pro Pro Gln Gly
                 85                  90                  95
Glu Asn Val Phe Phe Leu Val Thr Asn Phe Leu Val Thr Pro Ala Gln
                100                 105                 110
Val Gln Gly Arg Cys Pro Glu His Pro Ser Val Pro Leu Ala Asn Cys
         115                 120                 125
Trp Val Asp Glu Asp Cys Pro Glu Gly Glu Gly Thr His Ser His
130                 135                 140
Gly Val Lys Thr Gly Gln Cys Val Val Phe Asn Gly Thr His Arg Thr
145                 150                 155                 160
Cys Glu Ile Trp Ser Trp Cys Pro Val Glu Ser Gly Val Val Pro Ser
                165                 170                 175
Arg Pro Leu Leu Ala Gln Ala Gln Asn Phe Thr Leu Phe Ile Lys Asn
         180                 185                 190
Thr Val Thr Phe Ser Lys Phe Asn Phe Ser Lys Ser Asn Ala Leu Glu
         195                 200                 205
Thr Trp Asp Pro Thr Tyr Phe Lys His Cys Arg Tyr Glu Pro Gln Phe
 210                 215                 220
Ser Pro Tyr Cys Pro Val Phe Arg Ile Gly Asp Leu Val Ala Lys Ala
225                 230                 235                 240
Gly Gly Thr Phe Glu Asp Leu Ala Leu Leu Gly Gly Ser Val Gly Ile
                245                 250                 255
Arg Val His Trp Asp Cys Asp Leu Asp Thr Gly Asp Ser Gly Cys Trp
         260                 265                 270
Pro His Tyr Ser Phe Gln Leu Gln Glu Lys Ser Tyr Asn Phe Arg Thr
         275                 280                 285
Ala Thr His Trp Trp Glu Gln Pro Gly Val Glu Ala Arg Thr Leu Leu
 290                 295                 300
Lys Leu Tyr Gly Ile Arg Phe Asp Ile Leu Val Thr Gly Gln Ala Gly
305                 310                 315                 320
Lys Phe Gly Leu Ile Pro Thr Ala Val Thr Leu Gly Thr Gly Ala Ala
                325                 330                 335
Trp Leu Gly Val Val Thr Phe Phe Cys Asp Leu Leu Leu Tyr Val
                340                 345                 350
Asp Arg Glu Ala His Phe Tyr Trp Arg Thr Lys Tyr Glu Glu Ala Lys
         355                 360                 365
Ala Pro Lys Ala Thr Ala Asn Ser Val Trp Arg Glu Leu Ala Leu Ala
 370                 375                 380
Ser Gln Ala Arg Leu Ala Glu Cys Leu Arg Arg Ser Ser Ala Pro Ala
385                 390                 395                 400
Pro Thr Ala Thr Ala Ala Gly Ser Gln Thr Gln Thr Pro Gly Trp Pro
                405                 410                 415
Cys Pro Ser Ser Asp Thr His Leu Pro Thr His Ser Gly Ser Leu
         420                 425                 430
```